United States Patent
Diao et al.

(10) Patent No.: US 10,085,733 B2
(45) Date of Patent: Oct. 2, 2018

(54) ENDOSCOPIC SYSTEM FOR ACCESSING CONSTRAINED SURGICAL SPACES

(71) Applicant: Socorro Medical, Inc., San Francisco, CA (US)

(72) Inventors: Edward Diao, San Francisco, CA (US); Rajan Kashibhai Patel, Woodside, CA (US)

(*) Notice: Subject to any disclaimer, the term of this patent is extended or adjusted under 35 U.S.C. 154(b) by 256 days.

(21) Appl. No.: 14/733,828

(22) Filed: Jun. 8, 2015

(65) Prior Publication Data

US 2015/0265268 A1    Sep. 24, 2015

Related U.S. Application Data

(63) Continuation of application No. 12/328,678, filed on Dec. 4, 2008, now Pat. No. 9,050,004.
(Continued)

(51) Int. Cl.
| | |
|---|---|
| *A61B 17/02* | (2006.01) |
| *A61B 1/018* | (2006.01) |
| *A61M 25/09* | (2006.01) |
| *A61B 1/00* | (2006.01) |
| *A61B 1/04* | (2006.01) |
| *A61B 1/317* | (2006.01) |

(Continued)

(52) U.S. Cl.
CPC ...... *A61B 17/0218* (2013.01); *A61B 1/00085* (2013.01); *A61B 1/00087* (2013.01); *A61B 1/018* (2013.01); *A61B 1/04* (2013.01); *A61B 1/317* (2013.01); *A61B 17/0206* (2013.01); *A61M 25/09* (2013.01); *A61B 1/32* (2013.01); *A61B 5/4893* (2013.01); *A61B 5/6858* (2013.01); *A61B 2017/00296* (2013.01); *A61B 2017/00323* (2013.01); *A61B 2017/00367* (2013.01); *A61B 2017/00991* (2013.01); *A61B 2017/0225* (2013.01)

(58) Field of Classification Search
CPC ............ A61B 17/0206; A61B 17/0218; A61B 1/0098; A61B 1/018; A61B 1/317; A61B 1/00085; A61B 1/32; A61B 5/6858; A61B 5/4893

See application file for complete search history.

(56) References Cited

U.S. PATENT DOCUMENTS

| | | |
|---|---|---|
| 4,962,770 A | 10/1990 | Agee et al. |
| 4,963,147 A | 10/1990 | Agee et al. |

(Continued)

OTHER PUBLICATIONS

PCT International Search Report and PCT Written Opinion of the International Searching Authority, International Application No. PCT/US2008/085584, dated Apr. 15, 2009, 12 pages.
(Continued)

*Primary Examiner* — Anh Dang

(57) ABSTRACT

A retractor instrument for minimally invasive surgery may include a housing with a longitudinal axis, an arm extending from a distal end of the housing, and an actuation mechanism, wherein actuation of the actuation mechanism causes radial expansion of the arm relative to the longitudinal axis. The device may be adapted for use with an endoscope or arthroscope or may be an integral part of one such scope. A method of performing surgery in constrained areas within the body is also included and may be applicable to the carpal tunnel of a wrist and palm or the cubital tunnel of an elbow.

19 Claims, 32 Drawing Sheets

Related U.S. Application Data

(60) Provisional application No. 61/005,837, filed on Dec. 7, 2007, provisional application No. 61/066,675, filed on Feb. 22, 2008, provisional application No. 61/050,253, filed on May 5, 2008.

(51) Int. Cl.
*A61B 1/32* (2006.01)
*A61B 5/00* (2006.01)
*A61B 17/00* (2006.01)

(56) References Cited

U.S. PATENT DOCUMENTS

| | | |
|---|---|---|
| 5,029,573 A | 7/1991 | Chow |
| 5,089,000 A | 2/1992 | Agee et al. |
| 5,190,541 A | 4/1993 | Abele et al. |
| 5,269,290 A | 12/1993 | Barrett et al. |
| 5,306,284 A | 4/1994 | Agee et al. |
| 5,323,765 A | 6/1994 | Brown |
| 5,325,883 A | 7/1994 | Orr |
| 5,339,803 A | 8/1994 | Mayzels et al. |
| 5,354,302 A | 10/1994 | Ko |
| 5,358,496 A | 10/1994 | Ortiz et al. |
| 5,364,365 A | 11/1994 | Wortrich |
| 5,425,355 A | 6/1995 | Kulick |
| 5,480,408 A | 1/1996 | Chow |
| 5,578,051 A | 11/1996 | Mirza |
| 5,620,446 A | 4/1997 | McNamara et al. |
| 5,632,717 A | 5/1997 | Yoon |
| RE35,523 E | 6/1997 | Berger |
| 5,667,472 A | 9/1997 | Finn et al. |
| 5,667,473 A | 9/1997 | Finn et al. |
| 5,730,749 A | 3/1998 | Battenfield |
| 5,735,865 A | 4/1998 | Schaumann et al. |
| 5,782,747 A | 7/1998 | Zimmon |
| 5,814,064 A | 9/1998 | Daniel et al. |
| 5,857,961 A | 1/1999 | Vanden Hoek et al. |
| 5,928,137 A | 7/1999 | Green |
| 5,968,061 A | 10/1999 | Mirza |
| 5,968,064 A | 10/1999 | Selmon et al. |
| 5,984,939 A | 11/1999 | Yoon |
| 6,030,406 A | 2/2000 | Davis et al. |
| 6,086,528 A | 7/2000 | Adair |
| 6,179,852 B1 | 1/2001 | Strickland et al. |
| 6,387,043 B1 | 5/2002 | Yoon |
| 6,394,964 B1 | 5/2002 | Sievert, Jr. et al. |
| 6,685,630 B2 | 2/2004 | Sauer et al. |
| 6,685,717 B1 | 2/2004 | Ilic |
| 6,685,724 B1 | 2/2004 | Haluck |
| 6,746,462 B1 * | 6/2004 | Selmon .............. A61M 29/02 606/159 |
| 7,041,115 B2 | 5/2006 | Mirza et al. |
| 7,056,329 B2 | 6/2006 | Kerr |
| 7,179,225 B2 | 2/2007 | Shluzas et al. |
| 7,331,978 B2 | 2/2008 | Haluck |
| 7,988,619 B2 | 8/2011 | Longo et al. |
| 2002/0198551 A1 | 12/2002 | Grant et al. |
| 2003/0014065 A1 | 1/2003 | Osterlind |
| 2003/0032975 A1 | 2/2003 | Bonutti |
| 2004/0082969 A1 | 4/2004 | Kerr |
| 2004/0098005 A1 | 5/2004 | Mirza |
| 2004/0133228 A1 | 7/2004 | Bayer |
| 2005/0038423 A1 | 2/2005 | Makin et al. |
| 2005/0096501 A1 | 5/2005 | Stelzer et al. |
| 2006/0079925 A1 | 4/2006 | Kerr |
| 2006/0095028 A1 | 5/2006 | Bleich |
| 2006/0178554 A1 | 8/2006 | Mandel |
| 2007/0112366 A1 | 5/2007 | Welborn et al. |
| 2007/0129719 A1 | 6/2007 | Kendale et al. |
| 2007/0225740 A1 | 9/2007 | Suddaby |
| 2007/0288043 A1 | 12/2007 | Rehnke |
| 2008/0045989 A1 | 2/2008 | Welborn |
| 2008/0109020 A1 | 5/2008 | Grant et al. |
| 2008/0154293 A1 | 6/2008 | Taylor |
| 2008/0200758 A1 | 8/2008 | Orbay et al. |

OTHER PUBLICATIONS

Tsu-Min Tsai et al., "Cubital Tunnel Release With Endoscopic Assistance: Results of a New Technique", The Journal of Hand Surgery, vol. 24A No. 1, Jan. 1999, 11 pages.
US Non-Final Office Action for U.S. Appl. No. 12/328,678, dated Dec. 18, 2013, 7 pages.
US Non-Final Office Action for U.S. Appl. No. 12/328,678, dated Jun. 16, 2011, 26 pages.
US Final Office Action for U.S. Appl. No. 12/328,678, dated Oct. 10, 2014, 7 pages.
US Final Office Action for U.S. Appl. No. 12/328,678, dated Mar. 20, 2012, 10 pages.

* cited by examiner

ENDOSCOPIC SYSTEM FOR ACCESSING CONSTRAINED SURGICAL SPACES

CROSS-REFERENCE TO RELATED APPLICATIONS

This application is a continuation application of U.S. patent application Ser. No. 12/328,678 filed on 4 Dec. 2008 entitled "Endoscopic system for accessing constrained surgical spaces," which claims priority to U.S. Provisional Patent Application No. 61/005,837 filed on 7 Dec. 2007 entitled "Mechanically actuated rotational retractor having a protective sheath and method of displacing tissue to access constrained surgical spaces," U.S. Provisional Patent Application No. 61/066,675 filed on 22 Feb. 2008 entitled "Endoscopic system and method for ulnar nerve decompression in the cubital tunnel," and U.S. Provisional Application No. 61/050,253 filed on 5 May 2008 entitled "Surgical methods for decompressing nerves in the upper extremities," the contents of which are all hereby incorporated by reference herein in their entireties.

TECHNICAL FIELD

The following description relates to a medical apparatus and surgical methods. More specifically, the description relates to an instrument and to methods for minimally invasive surgical procedures in constrained spaces of the body. Even more particularly the description relates to a retractor instrument and methods for performing carpal tunnel release or ulnar nerve decompression procedures, or other related procedures.

BACKGROUND

Minimally invasive surgeries are well known and often involve an endoscopic or arthroscopic procedure where incisions are minimized and the surgery is performed within the body using one or more portals for insertion of instruments together with a camera or scope for viewing and conducting the procedure. Having avoided opening up the surface of the body, the surgical site may remain constrained by overlying tissues or other portions of the body that would have otherwise been lifted off of the site in an open procedure. These overlying portions of the body may obstruct or occlude access to the surgical site. Additionally, open and scope procedures alike may involve adjacent, overlying, or underlying tissues or other portions of the body that may obstruct or occlude access to the surgical site. Moreover, visualization may be limited due to over-crowding in certain constrained spaces or corporeal epicenters.

Several devices and methods are known in the art for facilitating access to a surgical site during endoscopic or arthroscopic procedures. These devices may include volumetric expansion devices such as inflatable retractors or other laterally expanding devices, such as slidable expanding sleeves. Methods may include tissue dissection.

Various problems or disadvantages can be found with these current options. Regarding inflatable retractors, they may not be effective in areas where the surrounding tissue is more rigid because the potential for sufficient volumetric expansion is not available. An additional concern is that inflatable retractors may be susceptible to rupture. A rupturing retractor can cause a sudden shift of instruments relative to anatomic structures which may damage anatomic structures such as blood vessels, nerves, other non-target structures, or even improperly damage the target structure. Moreover, a rupturing retractor may release a gas into the surgical site causing discomfort or even dangerous absorption into a blood vessel. The collapsing surgical site may leave the field obscured and the surgeon may not be aware of the damage caused. Additionally, depending on the extent of the rupture, portions of the retractor may even get lodged in crevices in the body. Regarding slidable expanding sleeves, positioning them once expanded can be difficult and may cause friction and abrasion of tissues. Regarding dissection, this approach is often not desirable because the obstructing tissue is healthy and because bleeding and/or scarring could cause further complications.

There is a need in the art for a device to displace tissue surrounding a surgical site rather than dissecting that tissue. Additionally, there is a need for the device to be capable of providing more net space when additional total space is not available. Moreover, there is a need for a device that allows for adjustability of the device and the tools used along with the device to appropriately access the surgical site.

SUMMARY

In one embodiment, a retractor instrument for minimally invasive surgery may include a housing with a longitudinal axis, an arm extending from a distal end of the housing, and an actuation mechanism, wherein actuation of the actuation mechanism causes radial expansion of the arm relative to the longitudinal axis. In another embodiment, the arm may include a ribbon like material with an integral hinge, wherein the ribbon returns radially inward toward the longitudinal axis and back upon itself at the integral hinge and further extends to an end. In another embodiment, the instrument may include a ring-like support structure with a center positioned approximately on the longitudinal axis, the end of the arm connected to the ring-like support structure. In another embodiment, advancing longitudinal motion of the arm together with limited longitudinal motion of the ring-like support structure may cause the hinge to open creating the radial expansion. In another embodiment, the instrument may include a sheath positioned on the arm and surrounding the arm. In another embodiment, the housing may be adapted to slidably receive a tubular body, the tubular body being allowed to rotate relative to the housing and the ring-like support structure. In still another embodiment, the tubular body may be an endoscope or arthroscope. In another embodiment, the arm may be a ribbed arm including a curved rib extending along a longitudinal length of the arm and directed radially inward toward the longitudinal axis. In another embodiment, the housing may include a tab and the ribbed arm may include a slit for receiving the tab, the ribbed arm being pivotally connected to the housing at the tab. In another embodiment, the instrument may include a sleeve with an outer surface slidably positioned within the housing, the sleeve adapted to receive a tubular body, the tubular body being allowed to rotate relative to the housing and ribbed arm. In another embodiment, the sleeve may be further adapted to allow telescopic motion of the tubular member beyond a distal end of the sleeve. In still another embodiment, the ribbed arms may be positioned such that advancing motion of the sleeve causes the outer surface of the sleeve to ride along an inner surface of the rib thereby expanding the ribbed arm radially outward.

In another embodiment, a medical instrument for minimally invasive surgery may include a tubular body in the form of an endoscope or arthroscope, the tubular body having a longitudinal axis, a proximal end, and a distal end, a sleeve slidably mounted on the tubular body, a housing having a distal end and a proximal end, the housing slidably mounted on the sleeve, a ribbed arm pivotally connected to the distal end of the housing, and an actuation mechanism where the actuation mechanism is configured to radially expand the ribbed arm relative to the longitudinal axis. In another embodiment, the tubular body may have an internal lumen for receiving and passing through a medical device. In another embodiment, the instrument may include a blade positioned within the lumen. In another embodiment, the blade may be a nitinol blade. In another embodiment, the tubular body may be rotatable relative to the housing to facilitate positioning of the blade without rotating the housing and the associated ribbed arm. In another embodiment, the ribbed arm includes a plurality of arms, the plurality of arms all pivotally connected to the distal end of the housing. In another embodiment, the plurality of ribbed arms may have a closed position and an open position, the arms defining an extension lumen in their closed position. In another embodiment, the arms may be positioned in a radial array around a perimeter of the distal end of the housing, the array having a number of equally spaced positions equal to the number of arms plus an additional position, the additional position adapted to increase the working space for the blade. In another embodiment, a non-ribbed arm may be included, wherein the non-ribbed arm and plurality of ribbed arms are equally spaced around a perimeter of the distal end of the housing.

In another embodiment, a method of performing surgery in a constrained area within a body may include making an incision in a patient, inserting a medical instrument through the incision, the medical instrument having a tubular body with an internal lumen and a blade extending there through, the tubular body surrounded by a housing and having at least one expandable arm connected to a distal end thereof, positioning the medical instrument adjacent to a surgical target structure, expanding the at least one expandable arm radially outward thereby displacing or protecting a non-target anatomical structure, extending the blade from a distal end of the tubular body, and cutting a portion of the surgical target structure with the blade. In another embodiment, the at least one expandable arm may include a plurality of expandable arms, the method further comprising positioning the blade relative to the expandable arms. In another embodiment, positioning the blade may include rotating the tubular body relative to the housing. In another embodiment, positioning the blade may include longitudinally moving the tubular body relative to the housing. In another embodiment, the medical instrument may further include a sleeve surrounding the tubular body and positioned between the tubular body and the housing, at least one guide wire connected to a proximal end of the at least one arm, and an actuation device for longitudinally advancing the sleeve and for selectively or collectively advancing the at least one guide wire connected to the at least one expandable arm, where the method further includes selectively actuating the actuation device thereby expanding the at least one expandable arm by advancing the sleeve or by advancing the guide wire. In another embodiment, the method may include advancing the tubular body beyond the distal end of the sleeve. In another embodiment, the method may include positioning the blade beyond the distal end of the expandable arms. In another embodiment, cutting an anatomical structure may include pushing the blade in a distal direction or pulling the blade in a proximal direction. In another embodiment, the tubular body may include at least one additional lumen, the method further including inserting a pressure sensing device and measuring a pressure before cutting and after cutting. In other embodiments, other diagnostic or therapeutic devices may be inserted.

In another embodiment, the constrained area in the method above may be a carpal tunnel of a wrist and palm. In another embodiment, the incision may be made in the wrist or the palm of a patient. In another embodiment, the surgical target structure is a transverse carpal ligament. In another embodiment, the non-target structure may be a median nerve.

In another embodiment, the constrained area in the method above may be a cubital tunnel of an elbow. In another embodiment, the incision may be made proximal to the cubital tunnel and slightly posterior to a medial epicondyle. In another embodiment, the medical instrument may include a visualization system and the method may further include identifying fascia of a posterior compartment at an elbow arising from an intramuscular septum, identifying an ulnar nerve, and using the ulnar nerve as a guide to direct the medical instrument along it. In another embodiment, the method may include determining which structures are touching or compressing the ulnar nerve under direct visualization. In another embodiment, the method may include manipulating or releasing the intramuscular septum and the fascia overlying the ulnar nerve. In another embodiment, the method may include reinserting or redirecting the medical instrument with its visualization system and one or more surgical instrument distally from the incision. In another embodiment, the method may include manipulating or releasing an Osborne's ligament, identifying fascia overlying a flexor carpi ulnaris muscle, dividing the fascia overlying the flexor carpi ulnaris muscle with the one or more surgical instrument to expose the underlying muscle. In another embodiment, the method may include performing perioperative electrodiagnostic and/or pressure studies pre-release and post-release of all structures. In another embodiment, the method may include moving the elbow through a range of motion while visualizing the ulnar nerve to determine if the ulnar nerve has a tendency to subluxate anterior to the medial epicondyle. In another embodiment, the method may include selectively performing a stabilization procedure if the ulnar nerve is found to have a tendency to subluxate. In another embodiment, the method may include using a mini-fluoroscopy x-ray machine to confirm identification of which structures are touching or compressing the ulnar nerve. In another embodiment, the method may include manipulating or releasing both a proximal portion and a distal portion of the flexor carpi ulnaris muscle.

While multiple embodiments are disclosed, still other embodiments of the present invention will become apparent to those skilled in the art from the following detailed description, which shows and describes illustrative embodiments of the invention. As will be realized, the invention is capable of modifications in various aspects, all without departing from the spirit and scope of the present invention. Accordingly, the drawings and detailed description are to be regarded as illustrative in nature and not restrictive.

DETAILED DESCRIPTION

The following detailed description relates to an instrument capable of use in endoscopic or arthroscopic surgical procedures. The instrument is directed at displacement and/or expansion of tissues in and around a surgical site such that the surgeon can see and carefully operate on target structures. The instrument is further directed at acute expansion of tissues such that it can be used in constrained spaces where overall or total expansion of a site is not feasible. That is, where the total volume is constrained by bones or other relatively rigid structures, the instrument may function to expand or displace the tissues proximately located to the instrument so as to allow access to target structures without expanding the total volume defined by the nearby rigid structure.

The following description includes a discussion of several of the procedures in which the instrument may be used. For example, the instrument may be used to perform carpal tunnel release (CRT) procedures to remedy symptoms associated with carpal tunnel syndrome. The instrument may also be used to perform ulnar nerve decompression to remedy symptoms associated with cubital tunnel syndrome. While the instrument may be adapted for constrained surgical spaces, the instrument may be used in most any surgery including open surgeries. Its use in an open surgery may facilitate learning such that a surgeon is more comfortable with the instrument and may then use the instrument during a closed endoscopic or arthroscopic procedure.

Figure 1:
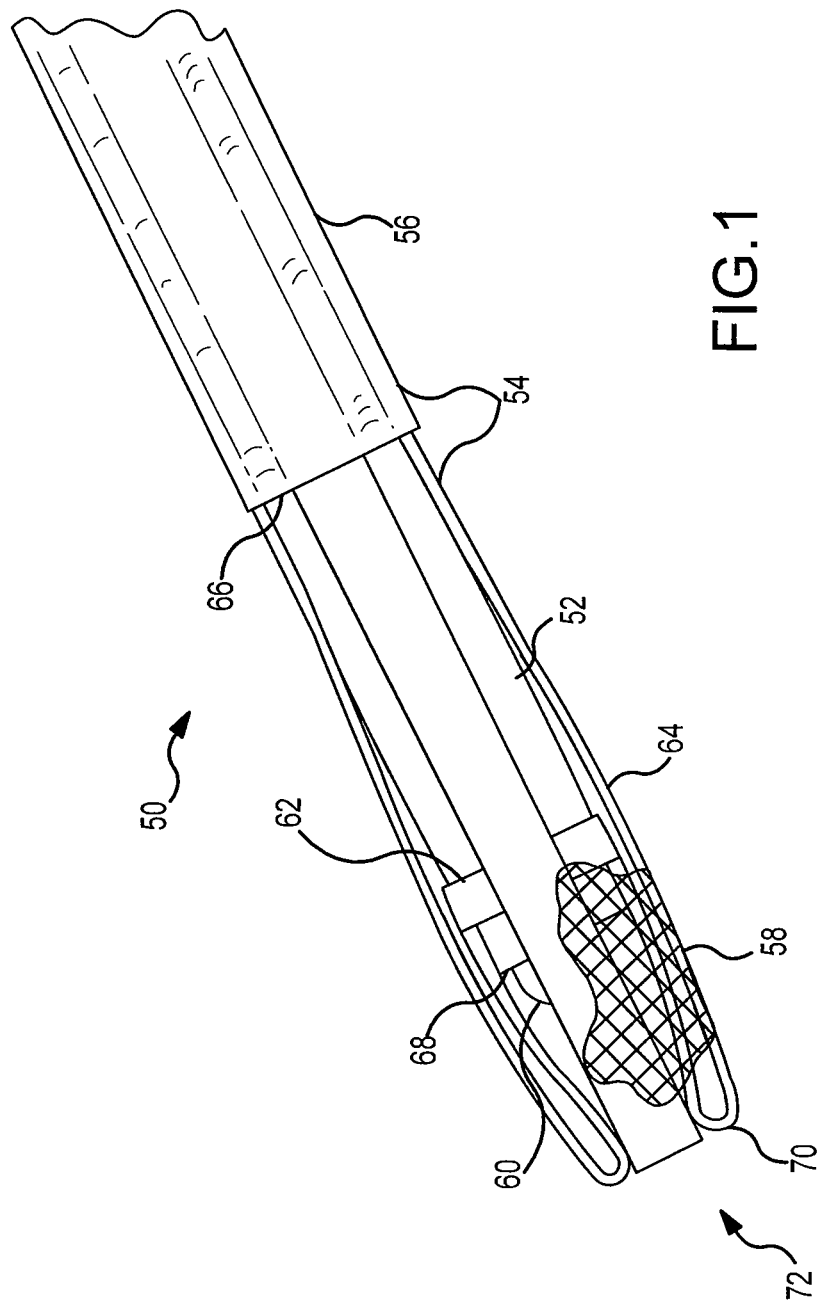
FIG. 1 is a side view of an instrument with arms in a closed position according to certain embodiments.

Referring now to FIGS. 1-7, a first embodiment of an instrument 50 is shown. FIG. 1 shows a tubular body 52, a skeletal sleeve 54, an outer housing 56, a protective sheath 58, a blade 60, and a ring-like support structure 62.

The skeletal sleeve 54 includes four expandable arms 64 that extend along the longitudinal length of the tubular body 52 and are surrounded in one portion by the outer housing 56 and in another portion by a protective sheath 58. As shown, the tubular body 52 extends beyond the distal end 66 of the outer housing 56. The arms 64 extend along the tubular body 52 in a distal direction, beyond the distal end 66 of the housing 56, and beyond the distal end 68 of the tubular body 52. The arms 64 then form an integral hinge 70 by turning radially inward and returning to the ring-like support structure 62 surrounding the tubular body 52. The arms 64 are slidable between the outer housing 56 and the tubular body 52 and are connected to the ring-like support structure 62. The ring-like support structure 62 is positioned near a distal end 68 of the tubular body 52 and is connected to the tubular body 52. The protective sheath 58 surrounds the arms 64 as they extend beyond the distal end 66 of the housing 56. The sheath 58 may fit around the arms 64 relatively loosely so as to accommodate expansion of the arms 64.

The housing 56 may include a flexible or rigid material with a smooth inner surface for allowing the arms 64 to slide readily against the inner surface. In contrast, the outer surface may have a knurled, patterned, or otherwise textured surface for providing a gripping surface. The housing 56 may fit relatively tightly around the tubular body 52 and the arms 64 to provide a circumferential compression force to resist buckling of the relatively thin arms 64 as they are advanced and contracted.

The arms 64 may be generally thin ribbons of elastic material. The ribbons may extend from an actuating device at a proximal end of the instrument 50 under the housing 56 and along the surface of the tubular body 52 to the distal end 72 of the instrument as shown in FIG. 1. The arms 64 may be made from an elastic material including stainless steel (e.g. #303 SST, #304 SST, and #316 SST), plastic including polycarbonate, or any other material capable of accommodating repeated motion between a collapsed position and an expanded position by including an integrated hinge 70.

The ring-like support structure 62 may be made from the same material as the arms 64 or may be a different material. The ring-like support structure 62 receives each of the arms 64, maintains their spacing, and controls the orientation of the arms 64 relative to the tubular body 52. The ring-like support structure 62 may be positioned near the distal end of the tubular body 52 and may be fixed to the tubular body 52. In another embodiment, the ring-like support structure 62 may be slidably engage the tubular body 52 and the tubular body 52 may include a stop preventing the ring-like support structure 62 from sliding off the end of the tubular body 52.

The sheath 58 may include a resilient mesh or membrane material. The sheath may also be an elastic type material such that it fits over the arms 64 relatively tightly, but also can accommodate expansion and contraction of the arms 64. The sheath 58 may be positioned over the series of arms 64 and stretch or extend from arm 64 to arm 64 in the form of a web or may be placed over each arm 64 individually. The sheath 58 may be positioned to protect the arms from entrance of tissue or debris in between the arms 64 and within the structure of the arms 64.

The tubular body 52 may be an endoscope, arthroscope, or other longitudinal member. The tubular body 52 may include an internal lumen or series of lumens 74. A port or series of ports 76 are positioned and define the distal end of the lumen or series of lumens 74 at the distal end 68 of the tubular body 52. These lumens 74 and associated ports 76 may be used for introducing devices for accessing the surgical site. As shown in FIG. 1, the distal tip of a blade 60 extends out the distal end 68 of the tubular body 52. Additionally, ports may be provided for visualization (i.e. fiber-optic) and illumination (i.e. laser) devices, imaging substances (i.e. radioactive isotopes and molecular imaging tracers), mechanical manipulation devices (i.e. graspers and scissors), therapeutic devices (i.e. a cryoprobe, delivery of medicines, electrical stimulators, etc.), pressure sensors, acoustoelastic sensors, and energy-emitting probes (i.e. emission of low frequency pulsed waves, radiofrequency waves, electromagnetic waves, shock waves, or laser waves). To increase the effectiveness of some of these devices, such as a fiber-optic video camera, the materials of the instrument within the viewing area may be made from transparent materials. For example, the tubular body 52, the arms 64, the housing 56, the sheath 58, and the ring-like support structure 62 may be made from clear or relatively transparent materials such as plastic or other known materials.

The outer profile of the arms 64 in their collapsed position may have a tapered shape to ease the insertion and withdrawal of the instrument 50. In this streamlined configuration, the diameter of the instrument 50 is smallest at the distal end 72 and gradually increases thereafter to a maximum value as the arms 64 approach the distal end 68 of the tubular body 52. At that point, the diameter decreases again to the point along the tubular body 52 where the arms 64 enter the housing 56. In addition to the tapered profile, the distal ends of the arms 64 may have a gently curved or rounded shape.

The arms 64 may have a length, measured from the point where they extend out of the housing 56 to their distal end in the collapsed position, between 3-5 mm, but this length may also be between 2-10 mm. The arms 64 may extend beyond the distal end 68 of the tubular body 52 and provide protection to the ports. Moreover, protecting the distal end 68 of the tubular body 52 may protect bodily structures from the blade 60 which may protrude slightly from one of the ports 76. In the collapsed position, the distance that the arms 64 extend beyond the tubular body 52 may depend on the stiffness of the arms 64 and their ability to maintain their shape as they extend beyond the tubular body 52. Moreover, this distance may depend on the desired size and profile of the expanded device. In one embodiment, this distance may be 2.5 mm.

The outer diameter of the skeletal sleeve 54 with the arms 64 in the collapsed position may range from 2-10 mm. In one embodiment, the skeletal sleeve 54 with collapsed arms 64 is approximately 3 mm in diameter and the arms 64, in their expanded position, may have a diameter of approximately 5.2 mm. The overall length of the instrument 50 may be from 5 cm to 32 cm.

Figure 2:
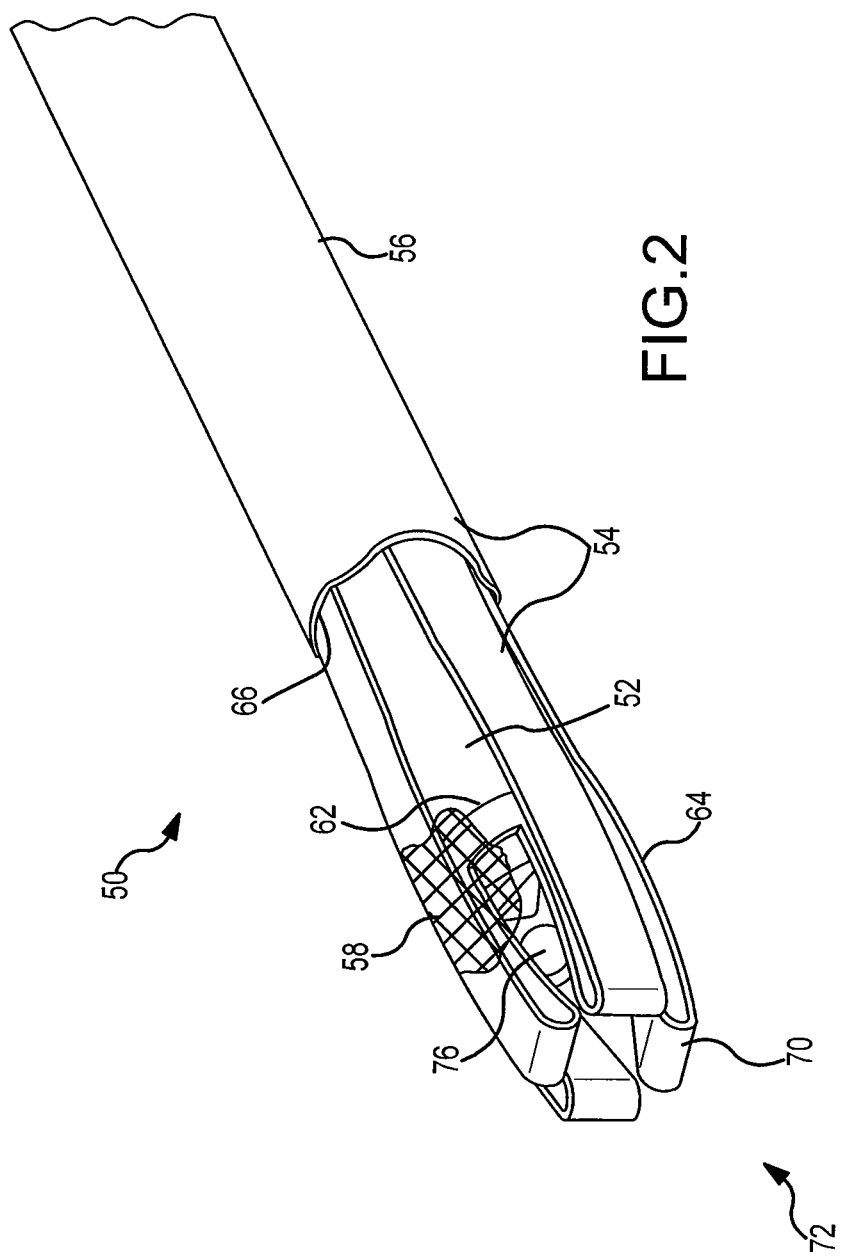
FIG. 2 is a distal side view of an instrument with arms in a closed position according to certain embodiments.

Referring now to FIG. 2, the distal tips of the arms 64 are shown. As shown, the distal tips of the arms 64 together form a perimeter around the space just beyond the distal end 68 of the tubular body 52. Each of the distal tips of the arms 64 forms a portion of this perimeter and, as shown, the perimeter further includes gaps between the distal tips. The protective sheath 58 as described may function to prevent tissue from becoming stuck to the arms 64 and in between the arms 64. Alternatively or additionally, fluid infusion, drain, insufflation, and aspiration ports 76 may be provided in the tubular body 52 to prevent tissue and other materials from becoming caught and/or to dislodge materials if they become caught between the arms 64 or within the folded structure of the arms 64.

Figure 3:
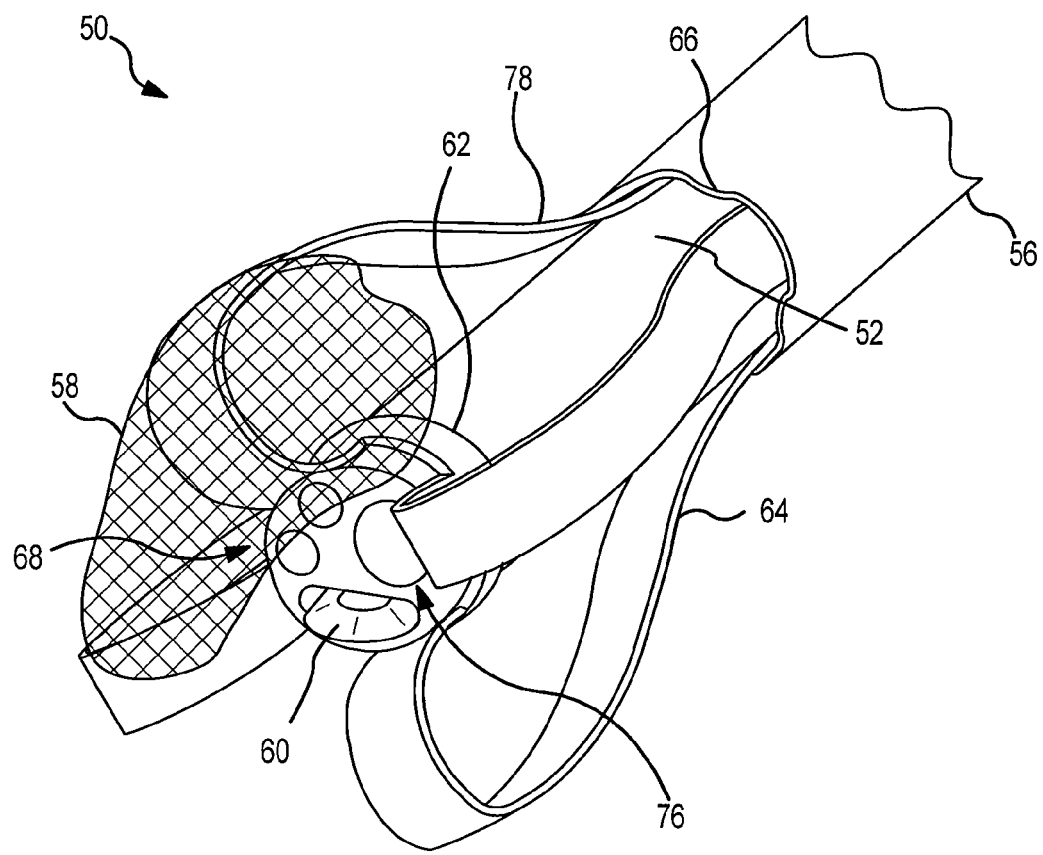
FIG. 3 is a distal side view of an instrument with arms in an open position according to certain embodiments.

Referring now to FIG. 3, the arms 64 are shown in an expanded position. In this position, the arms 64 have been advanced along the longitudinal length of the tubular body 52. Due to the limited distal movement of the distal ends of the arms 64 secured to the ring-like support structure 62, the ribbon like arms 64 have buckled outward due to the advancing force. This buckling occurs in the region beyond the distal end 66 of the housing 56, and not within the housing 56, because of the constraining force applied by the housing 56 along the length of the tubular body 52. In their expanded position the arms 64 form a generally concave curve as they extend out of the housing 56. As they continue to extend, the arms 64 include an inflection point 78 where they become convex and continue a smooth convex curve as the arms 64 return radially inward and proximally to the ring-like support structure 62. The material of the arms 64 discussed above together with the thickness and width of the arms 64 may be sufficient to displace tissue.

FIG. 3 shows four arms 64. Those skilled in the art will understand and appreciate that any number of arms 64 may be included and further that the arms 64 may be spaced uniformly or non-uniformly around the perimeter of the tubular body 52. As shown in FIG. 3, as the arms 64 expand, the space between the arms 64 increases due to their radial outward displacement. This space between the arms 64 may be a working space through which one or more devices, including graspers and blades 60, may pass to access target tissue. Where the arms 64 are spaced non-uniformly, the working space may not be the same between each arm 64. Moreover, the work space size may be controlled by using instruments 50 with larger or smaller spacings between arms 64. In embodiments where the protective sheath 58 surrounding the arms 64 forms a web between the expanded arms 64, sharp devices such as blades 60 may pass between the arms 64 by penetrating through the sheath 58. In embodiments where the sheath 58 closely conforms to the shape of each individual arm 64, open spaces between the arms 64 may permit devices to pass there between.

Figure 4:
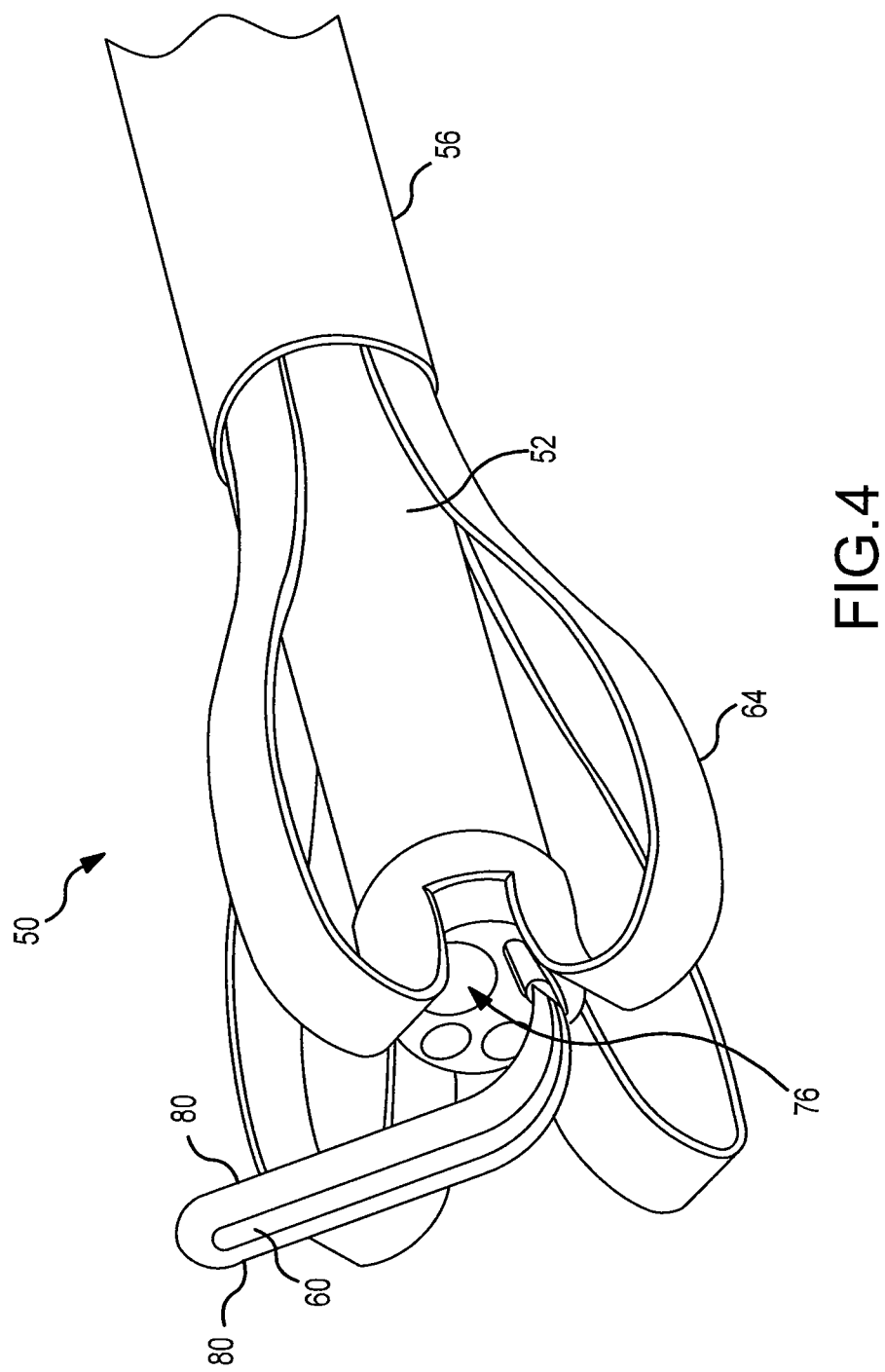
FIG. 4 is a distal side view of an instrument with arms in an open position and an extended blade according to certain embodiments.

Referring now to FIG. 4, the instrument 50 is shown in an expanded position with a steerable blade 60 extending out of a port 76 of the tubular body 52. The blade 60 may serve to cut or operate upon a target tissue while adjacent non-target structures are retained by the arms 64. The blade 60 may be made from a nickel titanium (nitinol) alloy or any other alloy displaying shape memory characteristics below its transformation temperature and superelastic characteristics above its transformation temperature. Stainless steel of the 400 series (e.g. #410 SST, #420 SST) may be a suitable material. Additionally, #440 SST may also be used to provide a hard, sharp, and durable cutting edge. A thicker blade 60 may be required in this instance due to the brittle nature of this material. Titanium may also be used.

A variety of blade styles may be used depending on an individual surgeon's preferred method and preferred direction of cutting. These may include a puncture knife, a reverse cut knife, a rasp, or a currette. The blade style may also include a pull blade, a push blade, a triangle blade, and a rasp. Those skilled in the art will understand and appreciate the several types of blades 60 known in the art and that the blade style used will depend on several factors including the site of the incision, the direction of cut, and whether the surgeon prefers to cut from below or above a particular structure.

The blade 60 shown extends longitudinally past the distal tips of the expanded arms 64 and then bends radially outward. The blade 60 may have a degree of curvature defined by a radius of a generally radial bend, the curve turning an angle of approximately 90 degrees. As shown, the cutting edge 81 of the distal tip of the blade is positioned transverse to the longitudinal direction of the instrument. All aspects of the blades orientation may be adjustable including the degree of curvature, the length of extension, and the direction of the cutting edge 81 of the distal tip. In addition, in some embodiments, the instrument 50 may be made steerable to facilitate accessing hard to reach surgical sites.

Figure 5:
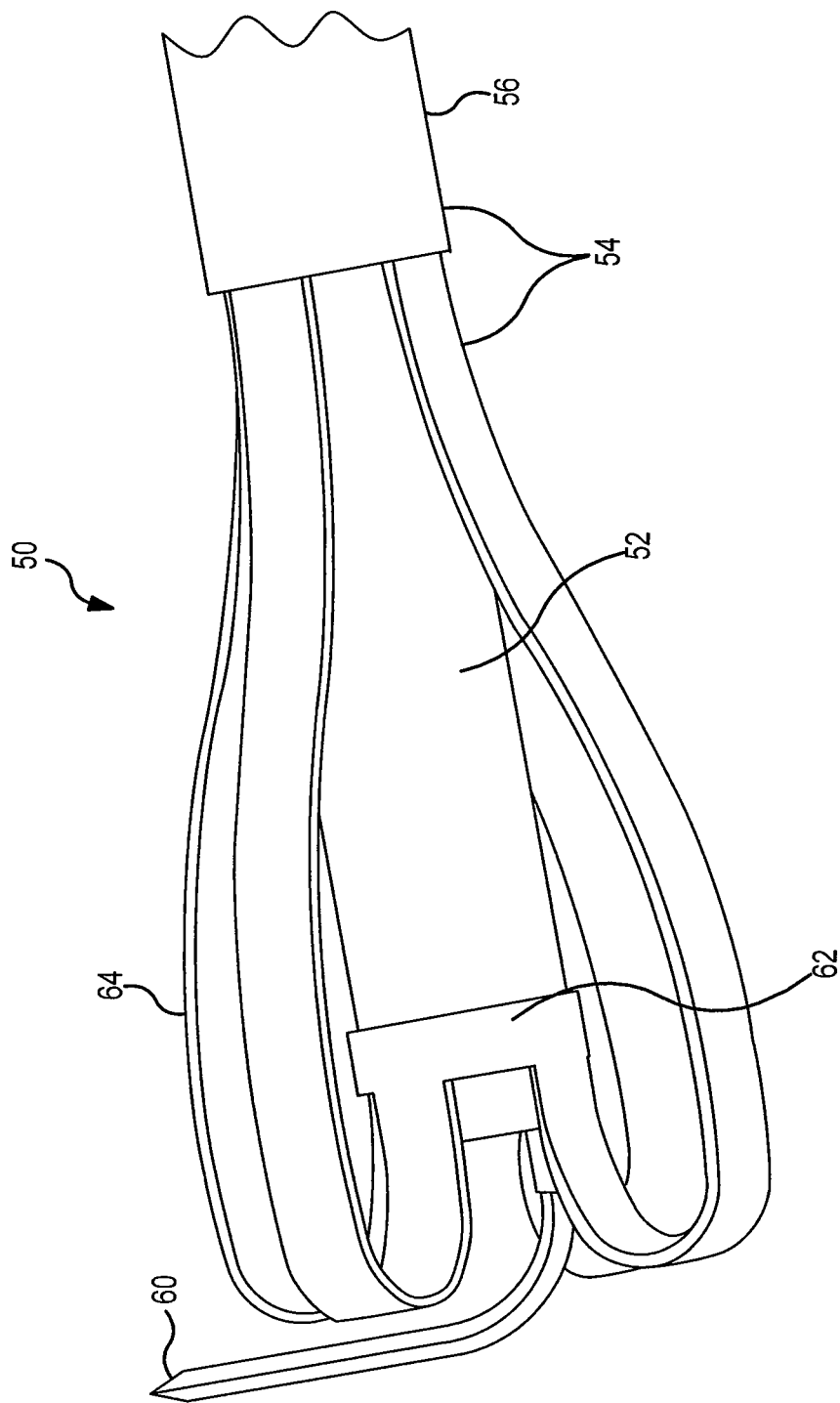
FIG. 5 is a side view of an instrument with arms in an open position and an extended blade according to certain embodiments.

Referring now to FIG. 5, a relatively high degree of curvature of a nitinol blade 60 is shown. As such, a nitinol blade 60 may form a 90 degree angle from its extension out of a port 76 of the tubular body 52 and thus position itself within the working space formed between the arms 64 or just distal to the distal ends of the arms 64. Moreover, the shape memory characteristics of nitinol below its transformation temperature permit a surgeon to adjust the orientation and curvature of the blade 60 internally. That is, if the default shape is desired, a means may be provided to enable the blade 60 to reach its transformation temperature in order to superelastically restore the original shape. The means may be a blade heating means that is operable either internally at the site of surgery or externally outside the body. The heating means may be part of the blade 60 or a separate component that transfers energy to the blade 60. In one embodiment, the heating means may be a heating wire within the body of the blade 60 where the wire is connected to a power source.

Figure 6:
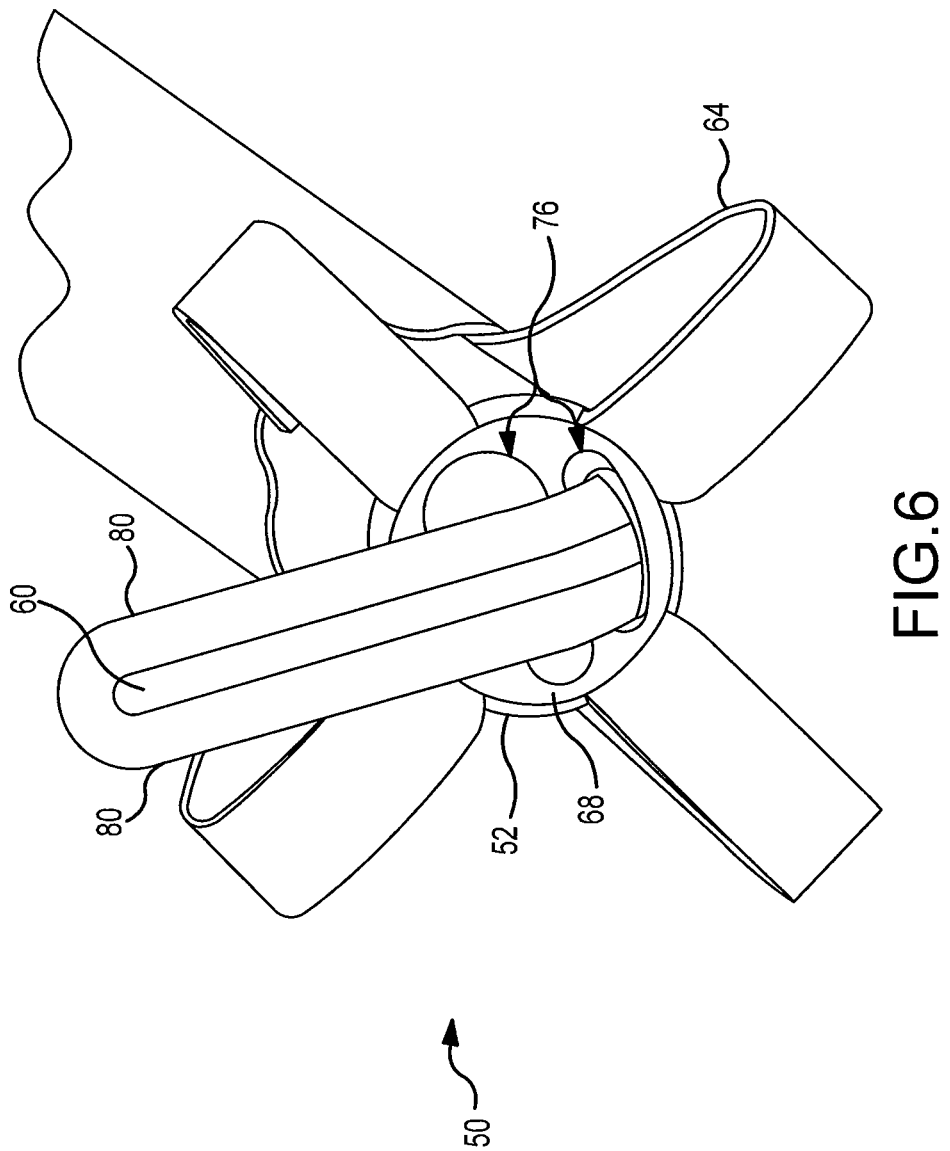
FIG. 6 is a distal view of an instrument depicting the orientation and relationship between a scope port and a cutting blade according to certain embodiments.

Referring now to FIG. 6, a distal view of the instrument 50 is shown. The blade 60 is shown in a position similar to that of FIG. 5 extending out of the tubular body 52 and bending to lie in a transverse position relative to the longitudinal length of the tubular body 52. Beyond the blade 60, several ports 76 are shown. In one embodiment, a scope port 76 is included and is positioned offset relative to the blade port 76 and blade position such that a view from the scope port 76 will show the proximal side of the blade 60 and the tissues or structures beyond the blade 60.

Figure 7:
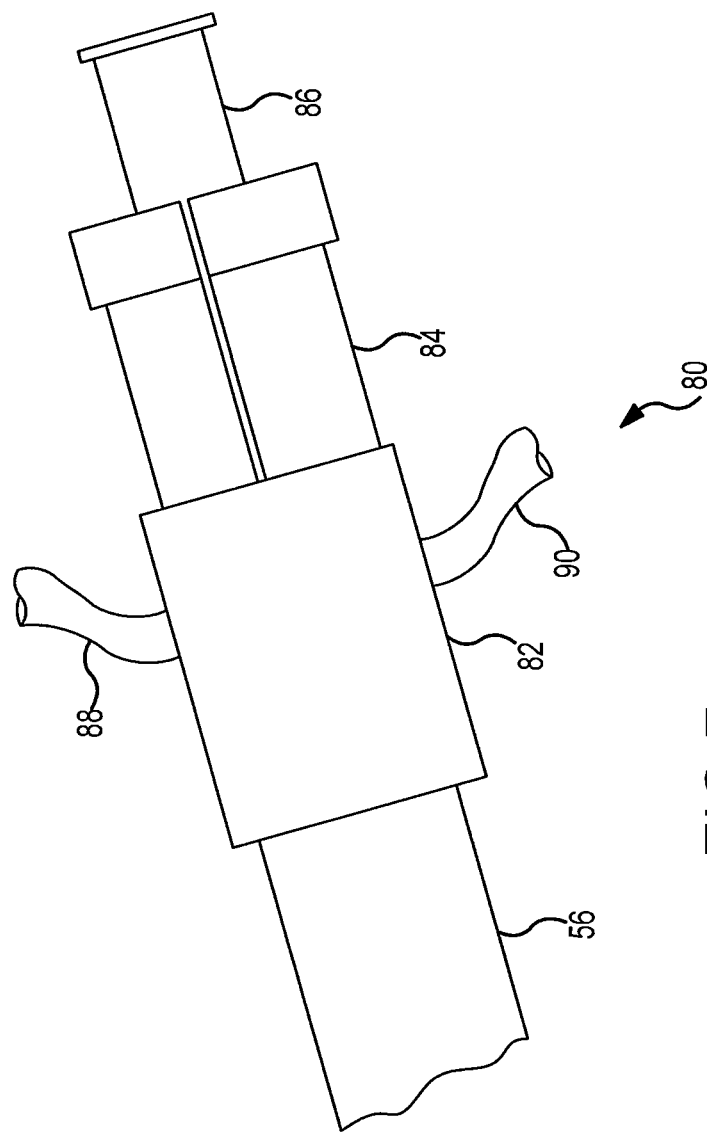
FIG. 7 is a side view of an actuation device for an instrument according to certain embodiments.

As mentioned with respect to FIG. 1 and shown now in FIG. 7, the arms 64 may extend from an actuating device 80 at a proximal end of the instrument 50 under the housing 56 and along the surface of the tubular body 52 to the distal end 72 of the instrument 50. As shown in FIG. 7, in one embodiment the actuation device 80 may include a handle portion 82, a plunger portion 84, and a push button portion 86. Also shown are a light source 88 and an information line 90 for a camera passing through the actuation device 80.

As shown, the handle 82 may be connected to the housing 56. The plunger portion 84 may be slidably and rotatably received by the handle 82 or may be threadably engaged with the handle 82. Additionally, the plunger portion 84 may be divided up into selective sections. The push button portion 86 may be slidably and rotatably engaged with the plunger portion 84 or may be threadably engaged.

The plunger portion 84 may be used to expand and contract the arms 64. That is, advancing the plunger 84, either through forced longitudinal motion, a screwing motion, or other known advancement methods, may cause the arms 64 to expand to their position shown in FIG. 4. The selective sections of the plunger portion 84 may be used to selectively expand the arms 64 rather than expanding or contracting all of the arms simultaneously. The plunger 84 may be locked in any position along its length of travel. The push button 86 may be used to advance and retract the blade 60. The push button 86 may also include several levels of advancement and may be locked in any of these positions. Once inserted, the device may allow for the blade 60 and the tubular body 52 to be rotated relative to the remaining portions of the instrument 50.

A locking mechanism, as mentioned, may be provided integral with the actuation device 80 or separately. The locking mechanism may be a screw with a continuous spectrum of lockable positions or a click-stop mechanism with discrete increments of lockable positions.

Figure 8:
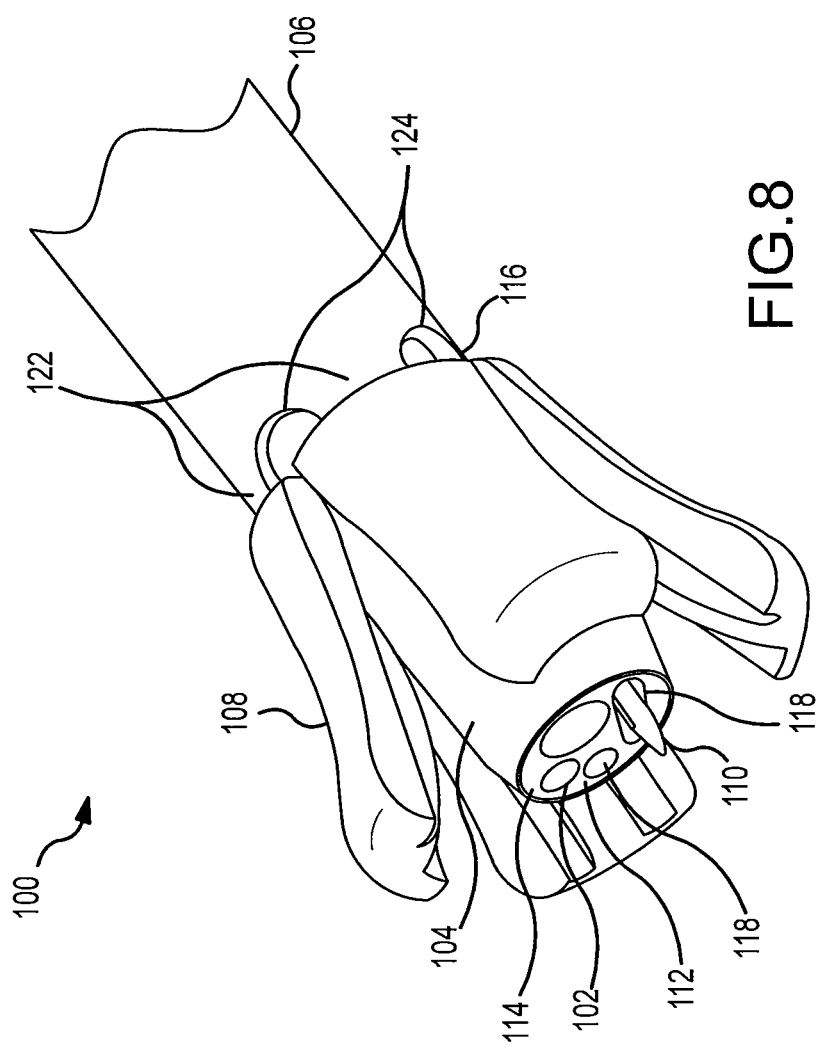
FIG. 8 is a perspective view of an instrument with arms in an expanded position according to certain embodiments.

Referring now to FIGS. 8-19, a second embodiment of an instrument 100 is shown. FIG. 8 shows a tubular body 102, a tapered sleeve 104, an outer housing 106, four ribbed retractor arms 108, and a blade 110 protruding from the tubular body 102.

The tubular body 102 is similar to that of the first embodiment. As shown, a blade 110 is protruding out of a port 118 of the tubular body 102. In this embodiment, a tapered sleeve 104 surrounds the tubular body 102 and extends over the longitudinal length of the tubular body 102. The tapered sleeve 104 slidably engages the tubular body 102 allowing for relative longitudinal telescoping movement between these two elements. As shown, the distal end 114 of the tapered sleeve 104 is positioned generally flush with the distal end 112 of the tubular body 102. The tapered sleeve 104 is surrounded by a housing 106. The housing 106 is positioned on the tapered sleeve 104 and allows for both sliding motion and rotational motion between these two elements. As shown, the distal end 116 of the housing 106 is positioned proximal to and exposing the distal ends 112, 114 of the tubular body 102 and the tapered sleeve 104. The ribbed retractor arms 108 are pivotally connected to the distal end 116 of the housing 106 and extend to the distal end 112, 114 of the tubular body 102 and the tapered sleeve 104. As shown the ribbed retractor arms 108 are uniformly spaced around the perimeter of the instrument 100 and are in an expanded position.

The tubular body 102 in this second embodiment is the same or similar to the tubular body 52 of the first embodiment and may be an endoscope, arthroscope, or other longitudinal member. The tubular body 102 may include one or a series of internal lumens 120 which form ports 118 in the distal end 112 of the tubular body 102. The lumens 120 are adapted for receiving and passing through various medical devices.

The tapered sleeve 104 has a generally annular shaped cross-section with an inner diameter substantially equal to an outer diameter of the tubular body 102. The outer diameter of the tapered sleeve 104 is generally constant over its length except at its distal end 114. Proximal to the distal end 114, the outer diameter of the tapered sleeved 104 steps down to a second outer diameter. At the stepped down location, the second outer diameter remains constant in a distal direction for a stub length and then decreases gradually over a taper length to the distal end 114. This stub length and taper length define the length of the distal tip of the tapered sleeve 104. In some embodiments, the sleeve 104 may include grooves on its outer surface for receiving ribs associated with the ribbed arms 108.

The outer housing 106, in this embodiment, is a generally annular shaped housing 106 with an inner diameter and an outer diameter. The inner diameter is substantially equal to the outer diameter of the tapered sleeve 104. The housing 106 extends along the longitudinal length of the instrument 100 and includes tabs 122 formed by U-shaped recesses 124 at its distal end 116. The tabs 122 are positioned around the perimeter of the distal end 116 of the housing 106 and are adapted to receive the ribbed arms 108.

Figure 9:
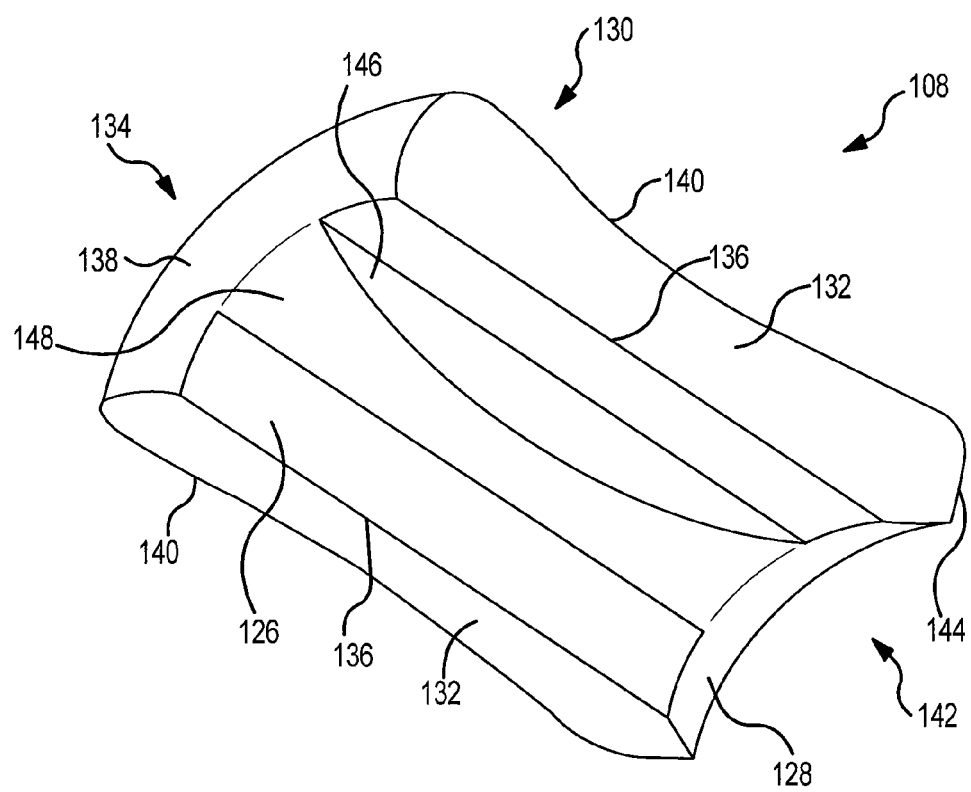
FIG. 9 is a perspective view of a proximal end and an inner surface of an arm according to certain embodiments.
Figure 10:
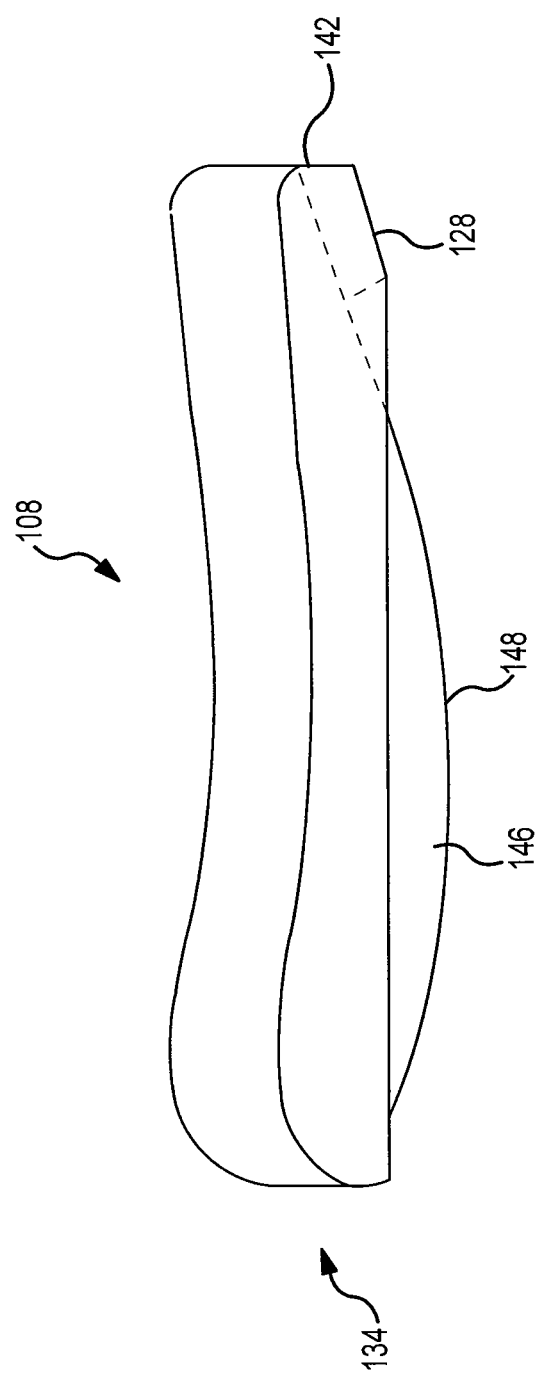
FIG. 10 is a side view of an arm according to certain embodiments.
Figure 11:
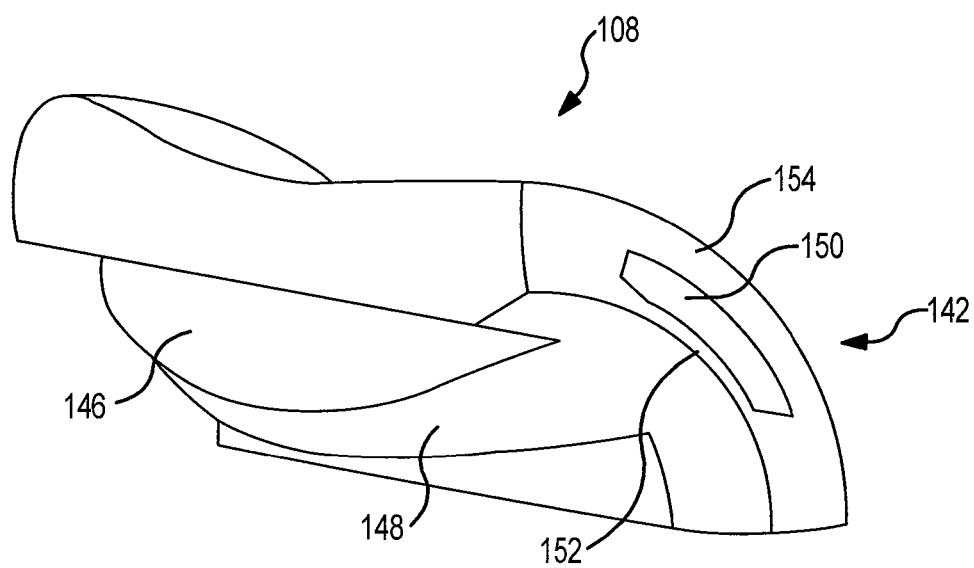
FIG. 11 is a perspective view of a distal end and an inner surface of an arm according to certain embodiments.

For a detailed discussion of the ribbed arms 108, reference is now made to FIGS. 9-11. Referring to FIG. 9, a ribbed arm 108 is shown. The arm 108 shown is generally shaped like a portion of a cylinder with an inner radius and an outer radius. The inner radius is generally constant along a longitudinal length of the arm 108 and along a radial arc of the arm 108. The constant inner radius defines an inner surface 126. At the proximal portion of the ribbed arm 108, the inner surface 126 forms a chamfered surface 128 over a length to its proximal end. In contrast to the constant inner radius, the outer radius varies along a longitudinal length of the arm 108, but any given radius along the longitudinal length is generally constant along a respective radial arc. The varying outer radius creates an outer surface 130 with a shape similar to an hour glass. That is, the radius to the outer surface 130 is larger near the proximal and distal ends than it is near the longitudinal center of the arm 108. The radius changes gradually throughout the longitudinal length creating a relatively smooth outer surface 130. On each lateral side of the ribbed arm 108 is an abutting face 132 adapted to abut or be spaced apart from an adjacent ribbed arm 108. The abutting faces 132 are generally flat faces connecting the inner surface 126 to the outer surface 130 where the inner edge 136 of the abutting faces 132 follows the profile of the inner surface 126 and outer edge 140 of the abutting faces 132 follow the profile of the outer surface 130. Each of the inner 136 and outer edges 140 form a relatively sharp corner with its respective intersecting surface. On the distal end of the ribbed arm 108, the outer surface 130 includes a smooth transition to the inner surface 126 creating a bull nose end 138. On the proximal end of the ribbed arm 108, the outer surface 130 includes a smooth but relatively abrupt transition to the inner surface 126 creating a relatively flat end 144 with a radiused outer edge.

Protruding from the inner surface 126 of the ribbed arm 108 is a longitudinally extending rib 146. The rib 146 extends from the distal end 138 of the arm to the proximal end 142 of the arm 108 and has a thickness in the transverse direction generally equal to the middle third of the transverse width of the inner surface 126. The rib surface 148 is a generally uniform surface defined by a varying quasi trapezoidal cross-section. The base of the quasi trapezoid follows the transverse curvature of the inner surface 126 of the arm 108. The sloping sides of the trapezoid are spaced apart and extend generally orthogonally from the inner surface 126 of the arm 108 in a converging manner. The sloping sides are truncated by the surface 148 of the rib 146 prior to converging with one another. The surface 148 of the rib 146 is generally flat in cross-section, but is defined by a radial arc in its longitudinal dimension. The arc is flush with the chamfered surface 128 at the proximal end 142 of the arm 108, increases to a maximum height near the longitudinal center of the arm 108 and decreases back down to the inner surface 126 at the distal end 134 of the arm 108.

FIG. 10 shows an additional view of the ribbed arm 108 depicting the profile of the rib 146 as it extends from the proximal end 142 of the arm 108 along the chamfered inner surface 128, arcs up, and then back down to the distal end 134 of the arm 108.

FIG. 11 shows a perspective view of the proximal end 142 of the ribbed arm 108 revealing a slit 150. The slit 150 is adapted to receive the tabs 122 at the distal end 116 of the housing 106. The connection between the tab 122 and the slit 150 is adapted to allow the ribbed arm 108 to pivot. The slit 150 includes a relatively narrow recess extending across the transverse width of the proximal end 142 of the arm 108. The slit 150 has a length adapted to accommodate the tab width on the housing 106. The slit 150 is further defined by an inner shell 152 and an outer shell 154. The step down portion of the tapered sleeve 104 discussed above is substantially equal to the thickness of the inner shell 152. That is, as the ribbed arm 108 is positioned on the tabs 122 of the housing 106 formed by the U-shaped notches 124, the inner shell 152 of the slit 150 encroaches on the tapered sleeve 104 due to the outer diameter of the sleeve 104 being substantially equal to the inner diameter of the housing 106. The stepped down outer diameter of the tapered sleeve 104 accommodates this inner shell thickness.

Figure 12:
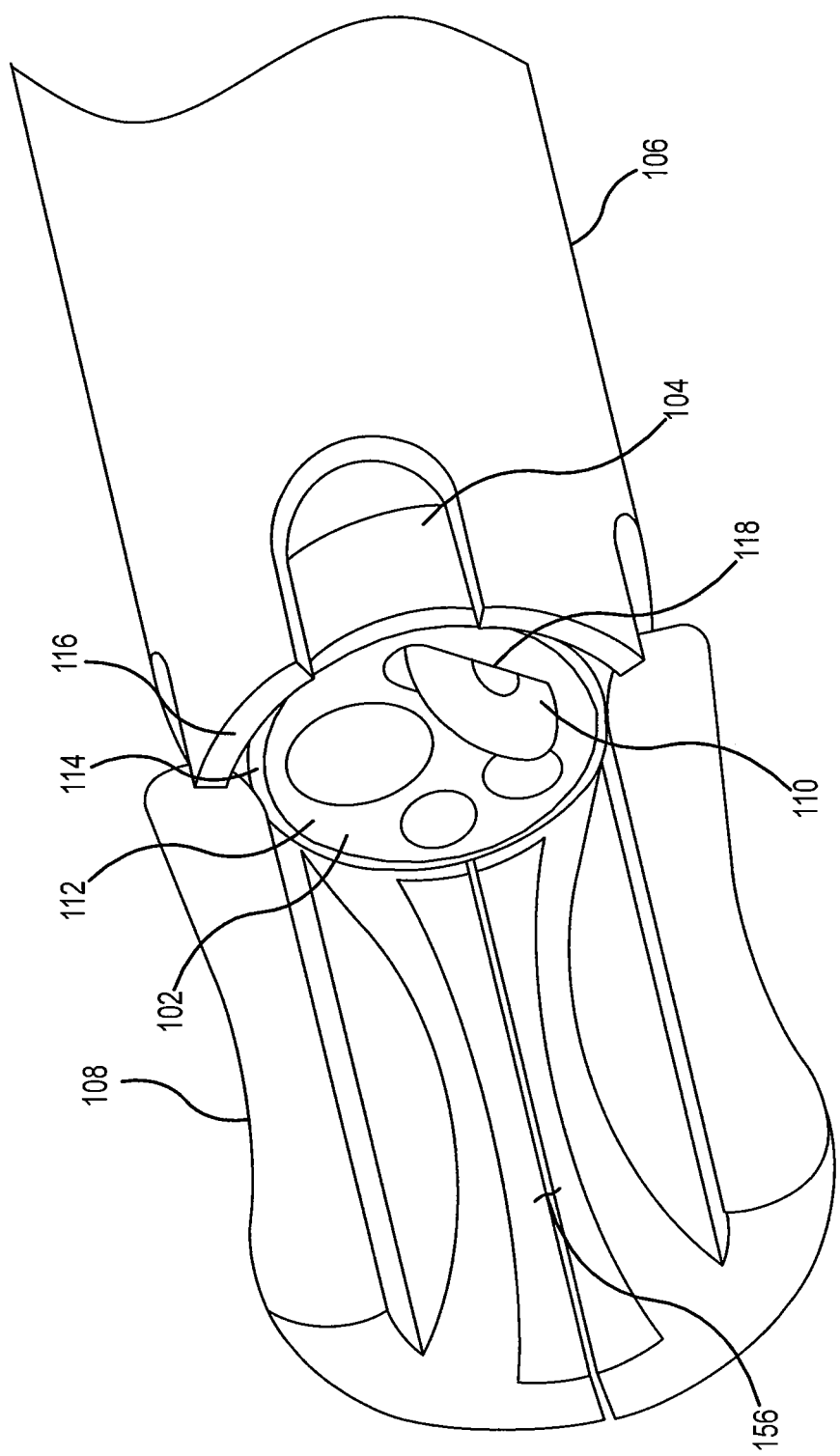
FIG. 12 is close-up view of an instrument in a closed position with a portion of the arms removed for purposes of explanation according to certain embodiments.

The actuation of the ribbed arms 108 may be understood from a review of FIGS. 12-15. FIG. 12 shows the distal end 112, 114 of the tubular body 102 and sleeve 104 both positioned approximately flush with the distal end 116 of the housing 106. Note that two of the ribbed arms 108 have been omitted for purposes of explanation. In this position, the ribbed arms 108 are in their closed or collapsed position and form an extension lumen 156 beyond the end of the tubular body 102 and sleeve 104. Also shown, is the distal tip of the blade 110 projecting slightly from a port 118 of the tubular member 102.

Figure 13:
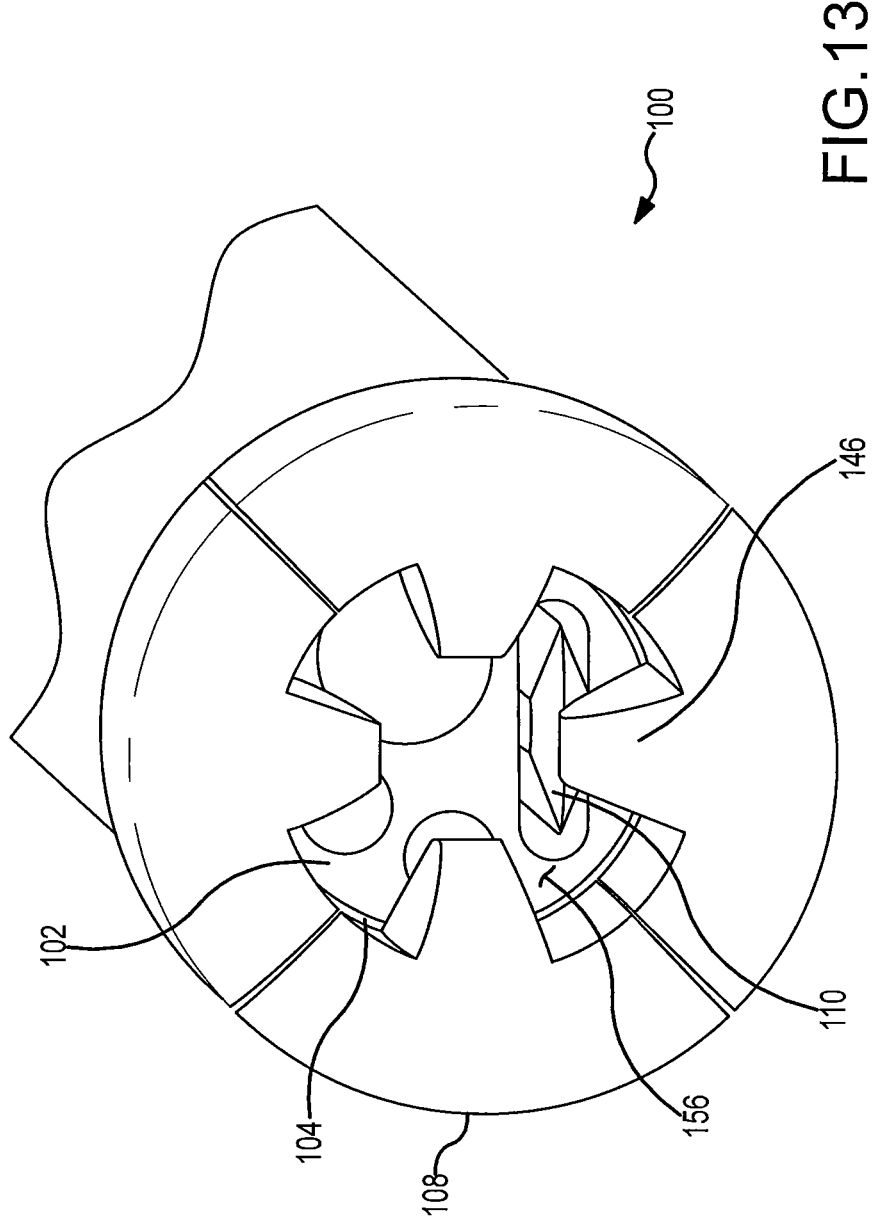
FIG. 13 is a close-up view of a distal end of an instrument depicting an extension lumen according to certain embodiments.

A distal view of this lumen 156 is shown in FIG. 13, where all of the ribbed arms 108 are in place. As shown, the extension lumen 156 has a diameter defined by the combined inner surfaces of the ribbed arms 108 and the lumen diameter is generally similar to the outer diameter of the sleeve 104. As also shown, the ribs 146 of the ribbed arms 108 project radially inward into the extension lumen 156. In this position, the instrument 100 is poised for insertion and withdrawal from a surgical site. The smooth outer surface of the ribbed arms 108 may allow for smooth insertion, while the position of the ribbed arms 108 relative to the blade 110, tubular body 102, and sleeve 104, provides protection from tissue intrusion into and around these elements. This protection may be buttressed by the ribs 146 extending into the extension lumen 156 providing additional protection against the intrusion of tissue or debris.

Figure 14:
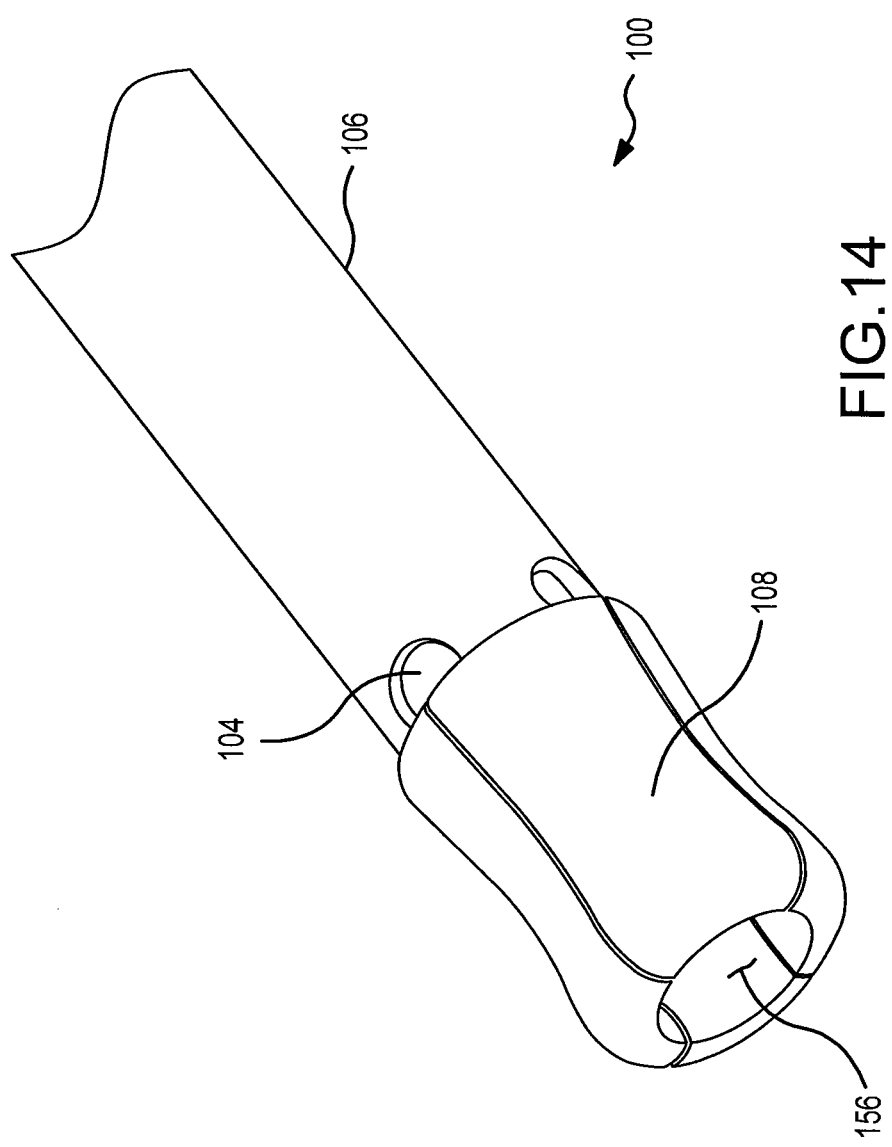
FIG. 14 is a perspective view of an instrument with arms in a closed position according to certain embodiments.

An external perspective view of the instrument 100 with the ribbed arms 108 in the closed or collapsed position is shown in FIG. 14. As shown, the outer diameter of the arms 108 may be small enough to approximate the outer diameter of the housing 106. The gently curved edges of the arms 108 may allow for adjustment of the position of the arms 108 once the instrument 100 is inserted without harming anatomical structures in their vicinity.

Figure 15:
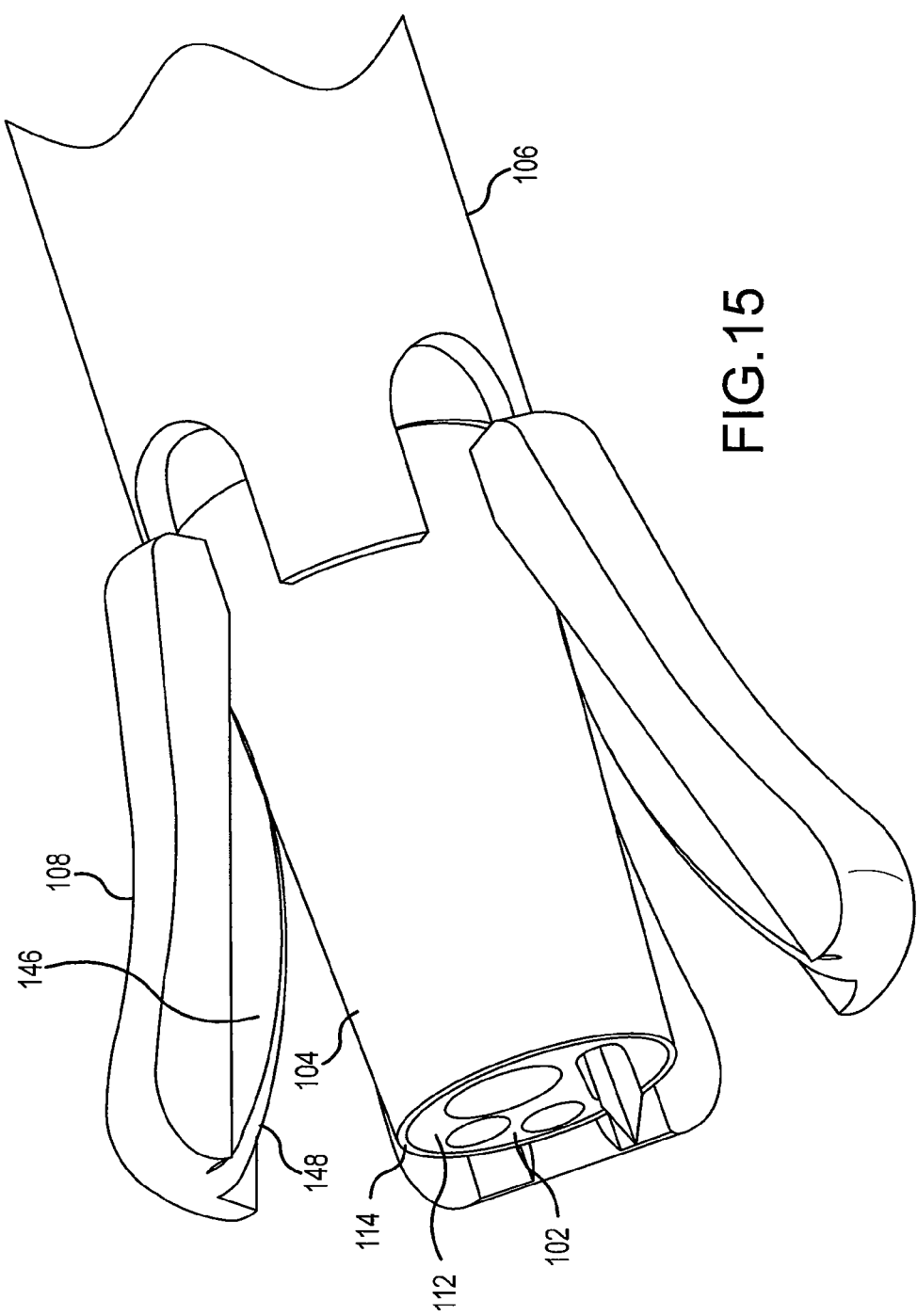
FIG. 15 is a close-up side view of a distal end of an instrument with an arm removed for purposes of explanation according to certain embodiments.

Referring now to FIG. 15, the distal end 112, 114 of the tubular body 102 and sleeve 104 have been telescopically slid in a distal direction and are approximately flush with the distal ends of the arms 108. It is noted that one of the ribbed arms 108 has been omitted for purposes of explanation. The progression of the tubular body 102 and sleeve 104 through the extension lumen 156 has pivotally displaced the ribbed arms 108 into their expanded or open position. That is, as the tubular arm 102 and sleeve 104 telescope out of the housing 106 and slide through the extension lumen 156, the outer surface of the sleeve 104 engages the surface of the rib 146 of each ribbed arm 108 and slides along the surface of the rib 146. The arc profile of the rib 146 and its position within the extension lumen 156 causes the ribbed arm 108 to rotate about its connection with the housing 106 to the open position shown. Moreover, the tapered nature of the distal tip of the sleeve 104 makes for a smooth transition that avoids hang ups. It is also noted that the stepped down portion of the sleeve 104 can been seen in this view, just proximal to the proximal end of the ribbed arms 108. As shown, the outer diameter of the sleeve 104 fits snugly within the housing 106 and the stepped down portion accommodates the inner shell 152 of the slits 150 of the ribbed arms 108 positioned to the inside of the housing tabs 122.

Those skilled in the art will understand and appreciate that various rib profiles, different from the one shown in FIG. 10, would be suitable including linearly increasing, or parabolic, or elliptical, or any other profile desired and that these additional profiles are within the scope of the invention. It is noted that the chosen profile may have an effect on the transition of the ribbed arms 108 as they displace between an expanded and contracted position and that the chosen profile may be selected based on its effect on this transition. For example, a more abrupt transition may be provided where the rib profile extends radially inward quite rapidly as it extends from its proximal end. Those of skill in the art will understand the several profiles available and their effect on the transition between an expanded or contracted position.

Further affecting the actuation of the ribbed arms 108 is whether the sleeve 104 includes grooves for receiving the ribs 146. That is, where grooves are included in the outer surface of the sleeve 104, the ribs 146 of the ribbed arms 108 may nest in the groove thereby guiding the sleeve 104 and preventing relative radial motion between the sleeve 104 and the ribbed arms 108 and housing 106. However, as the sleeve 104 is advanced, and the tapered length of the sleeve 104 passes along the ribs, the ribbed arms 108 may be radially actuated. Where the tapered length of the sleeve 104 is fully advanced, the ribbed arm 108 may be expanded to a point where the chamfered surface 128 of ribbed arm 108 comes into contact with the outer surface of the sleeve 104.

At this point, the rib 146 of the ribbed arm 108 may be lifted out of the groove on the sleeve 104 and allow for rotation of the ribbed arms 108 and housing 106 relative to the sleeve 104.

Figure 16:
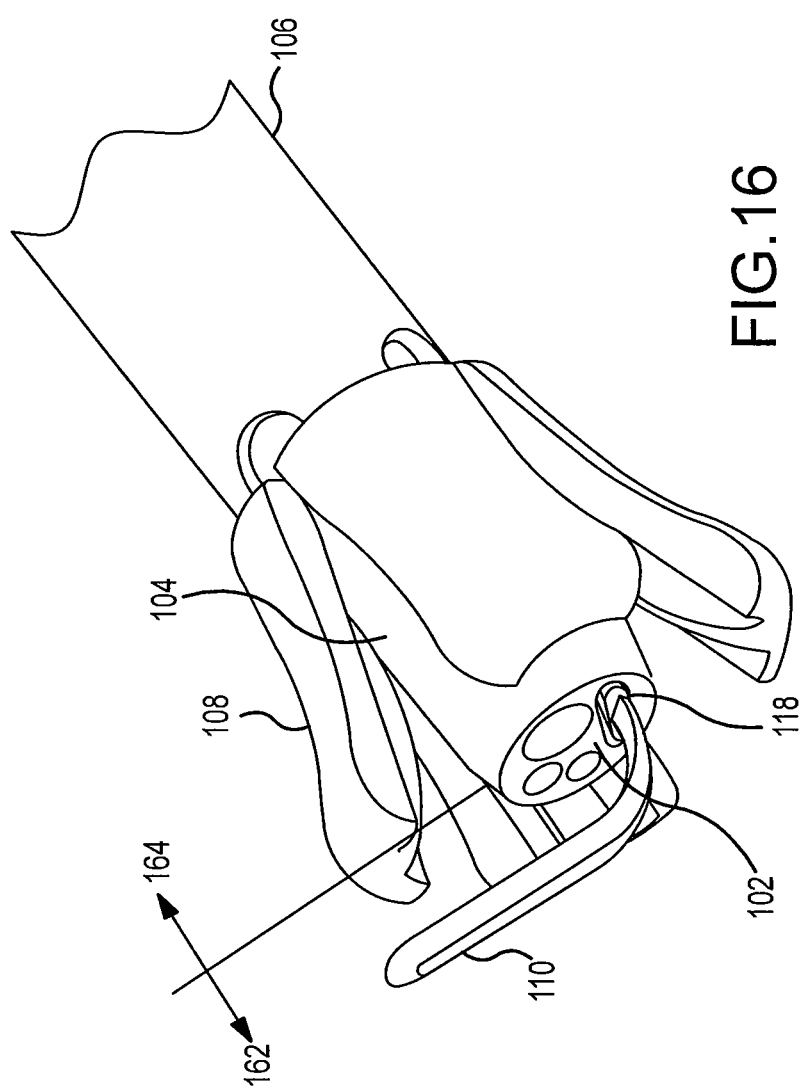
FIG. 16 is a perspective view of an instrument with arms in an open position and a blade in an extended position according to certain embodiments.

Referring now to FIG. 16, the blade 110 is shown extended out of a port 118 of the tubular body 102. As shown, the blade 110 is relatively long and includes a relatively high degree of curvature. In some embodiments the degree of curvature may be less than that shown and thus the blade 110 may extend at an angle somewhere between the distal longitudinal direction and the transverse direction. In other embodiments, the degree of curvature may be greater than that shown and thus the blade 110 may extend at an angle between the proximal longitudinal direction and the transverse direction. That is, the blade 110 may extend from the port 118 and turn so as to begin returning in the proximal direction.

Similar to that of FIG. 15, the distal end 112, 114 of the tubular body 102 and sleeve 104 in FIG. 16 are shown substantially flush with the distal end of the arms 108. As such, depending on the length and curvature of the blade 110 discussed above, the working space 160 for the blade 110 may include the space 162 distal to the distal end 112 of the tubular body 102 as well as the space 164 proximal to the distal end 112 of the tubular body 102 between the ribbed arms 108.

Figure 17:
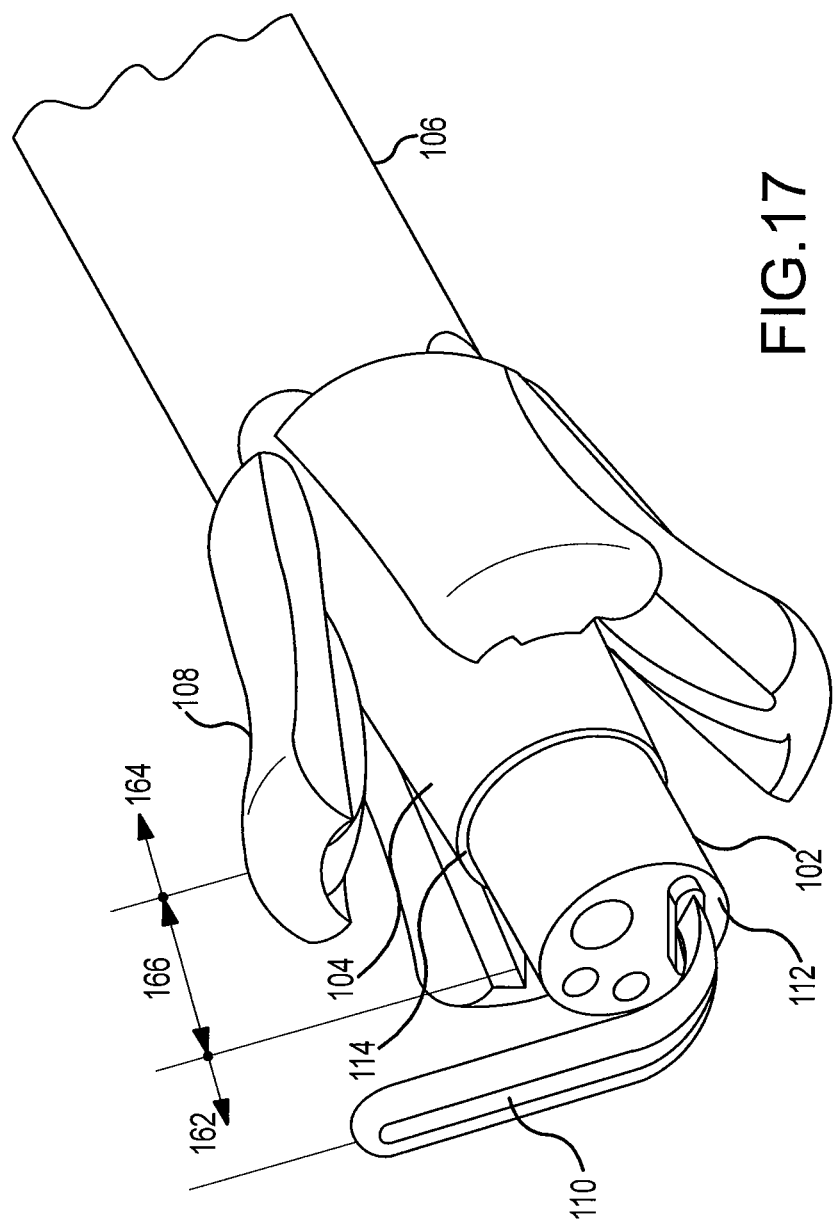
FIG. 17 is a close-up perspective view of a distal end of an instrument with arms in an open position, a blade in an extended position, and a tubular body projecting in a distal direction according to certain embodiments.
Figure 18:
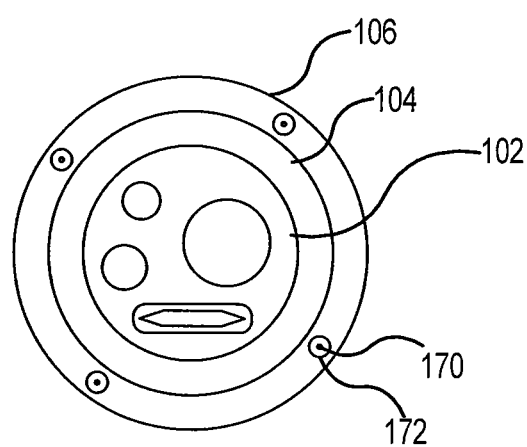
FIG. 18 is a cross-section view of an instrument depicting the guide wires for actuating arms of the instrument according to certain embodiments.

FIG. 17 shows yet another position of the tubular body 102, where the distal end 112 of the tubular body 102 is positioned distally to the distal end 114 of the sleeve 104 and the distal ends of the ribbed arms 108. In this position, again depending on the length and curvature of the blade 110, the working space 160 for the blade 110 still includes the space 162 distal to the distal end 112 of the tubular body 102 but also includes a full circumferential space 166 proximal to the distal end 112 of the tubular body 102 and distal to the distal ends of the sleeve 104 and the ribbed arms 108. If the curvature of the blade 110 and its length are sufficient, the working space 160 in this position may still include the space 164 between the ribbed arms 108.

It is noted that selective actuation as well as actuation of all of the ribbed arms 108 may alternatively be achieved by advancing a guide wire 170 connected to each of the ribbed arms 108 in lieu of advancing the sleeve 104. As shown in the cross-section view of FIG. 18, lumens 172, or alternatively surface recesses, may be included within the wall of the housing 106. The guide wire 170 may be actuated through longitudinal motion and may be connected to the inner shell 152 of the ribbed arm, such that advancing the guide wire 170 causes the ribbed arm 108 to expand by rotating about its connection to the tab 122 on the housing 106.

Figure 19:
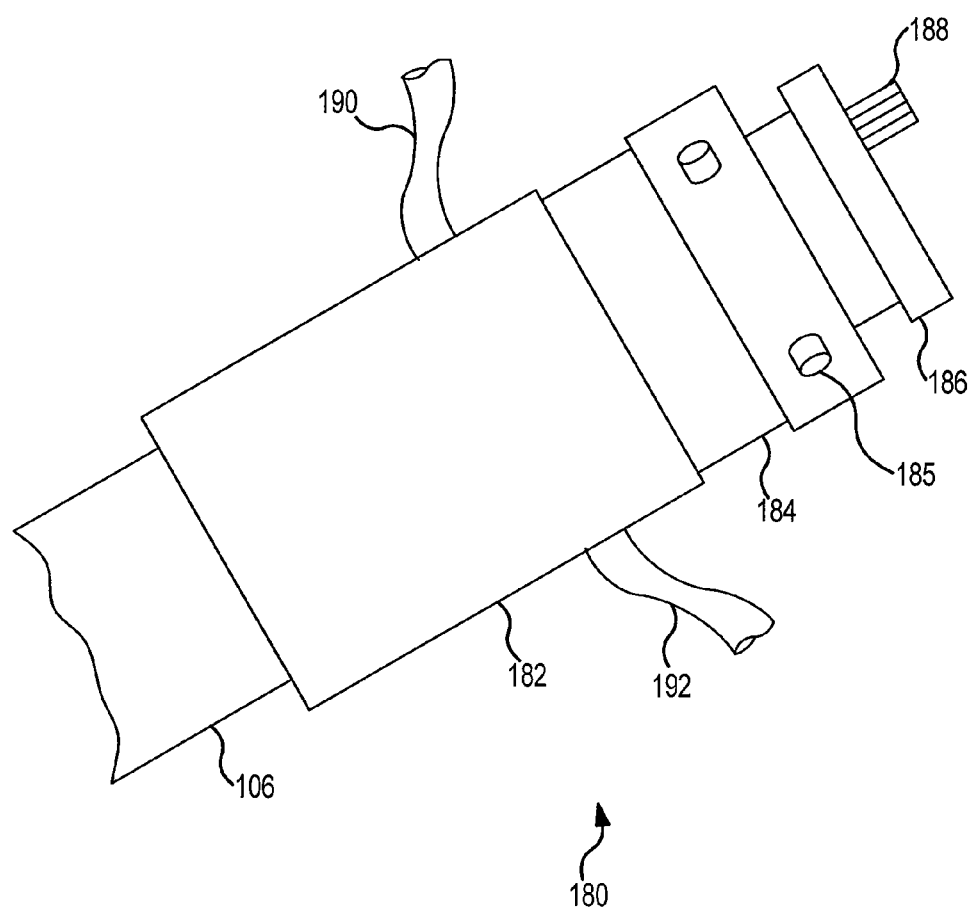
FIG. 19 is a side view of an actuation device for an instrument according to certain embodiments.

Similar to the actuating device 80 shown in FIG. 7, FIG. 19 shows an embodiment of an actuation device 180, which may include a handle portion 182, a sleeve actuator 184, a tubular body actuator 186, and a blade actuator 188. Also shown are a light source 192 and an information line 190 for a camera passing through the actuation device 180.

As shown, the handle 182 may be connected to the housing 106. The sleeve actuator 184 may be slidably and rotatably received by the handle 182 or may be threadably engaged with the handle 182. Additionally, the sleeve actuator 184 may include push button guide wire actuators 185. The tubular body actuator 186 may be slidably and rotatably engaged with the sleeve actuator 184 or may be threadably engaged. Additionally, a blade actuator 188 in the form of a push button or a turnable knob may be provided.

The sleeve actuator 184 may be used to expand and contract the arms 64. That is, advancing the sleeve actuator 184, either through forced longitudinal motion, a screwing motion, or other known advancement methods, may cause the arms 64 to expand to their position shown in FIG. 16 due to the rib 146 of the ribbed arm 108 riding along the surface of the sleeve 104. The sleeve actuator 184 may be locked in any position along its length of travel. The push button guide wire actuators 185 may be used to selectively expand the ribbed arms 108 rather than expanding or contracting all of the arms 108 simultaneously by advancing the sleeve 104. The guide wire actuators 185 may be depressed to selectively advance the guide wires 170 leading to the inner shell 152 of ribbed arm 108 thereby selectively expanding the arms 108. The guide wire actuators 185 may be locked in any position to control the expansion of the corresponding ribbed arm 108. The tubular body actuator 186 may be used to advance and retract the tubular body 102 from the sleeve 104. The tubular body actuator 186 may be free to move longitudinally and rotationally, such that when the instrument 100 is in place, the blade 110 may be positioned as needed without having to adjust the entire instrument 100. The tubular body actuator 186 may also include a blade actuator 188 in the form of a push button. The blade actuator 188 may include several levels of advancement and may be locked in any of these positions.

A locking mechanism, may be provided integral with any portion of the actuation device 180 or separately. The locking mechanism may be a screw with a continuous spectrum of lockable positions or a click-stop mechanism with discrete increments of lockable positions.

Figure 20:
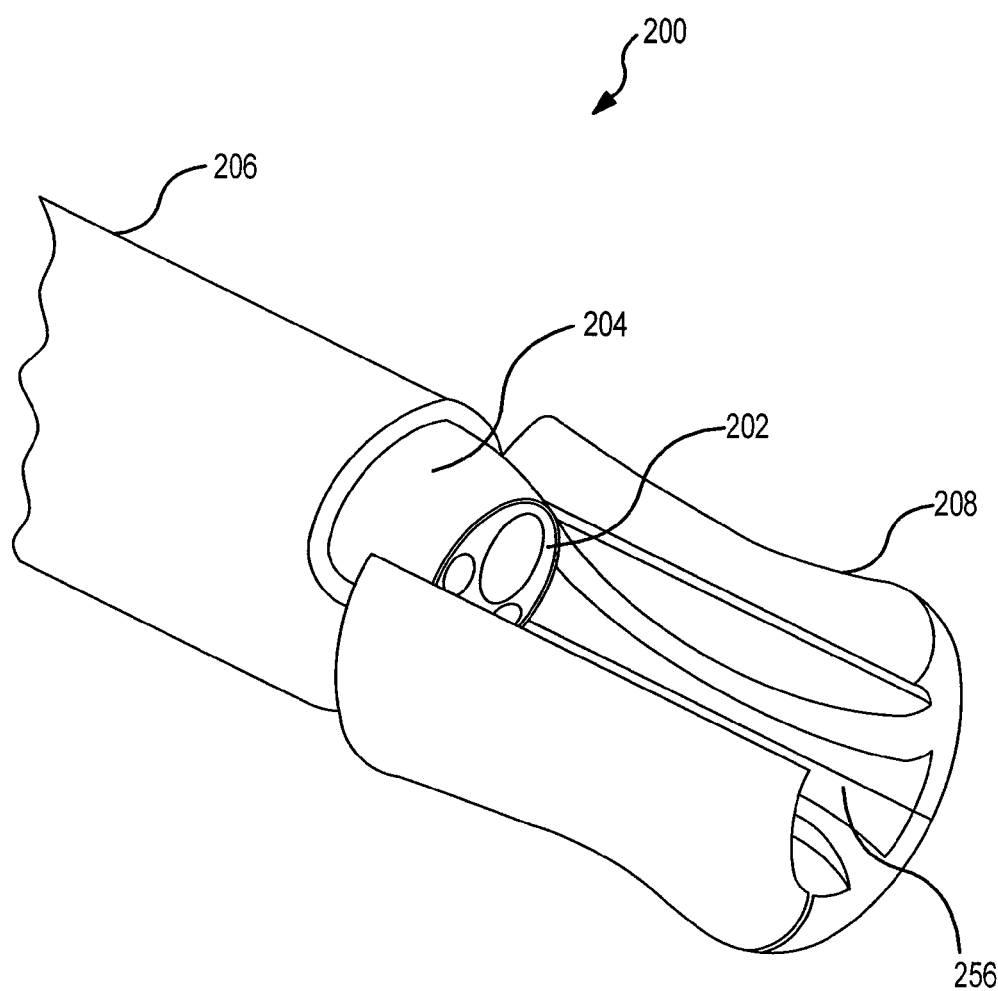
FIG. 20 is a perspective view of an instrument with an arm omitted and the arms in a closed position according to certain embodiments.

FIGS. 20-25 show yet another embodiment where one of the ribbed arms 208 have been omitted. FIG. 20 shows the instrument 200 with the ribbed arms 208 in the closed position. In this embodiment, the ribbed arms 208 each reflect approximately a quarter of the circumference of the instrument 200. One of the otherwise four ribbed arms 208 has been omitted and the associated tab 222 on the housing 206 has also been omitted. With one of the ribbed arms 208 omitted, a portion of the extension lumen 256 is exposed even with the arms 208 in the closed position.

Figure 21:
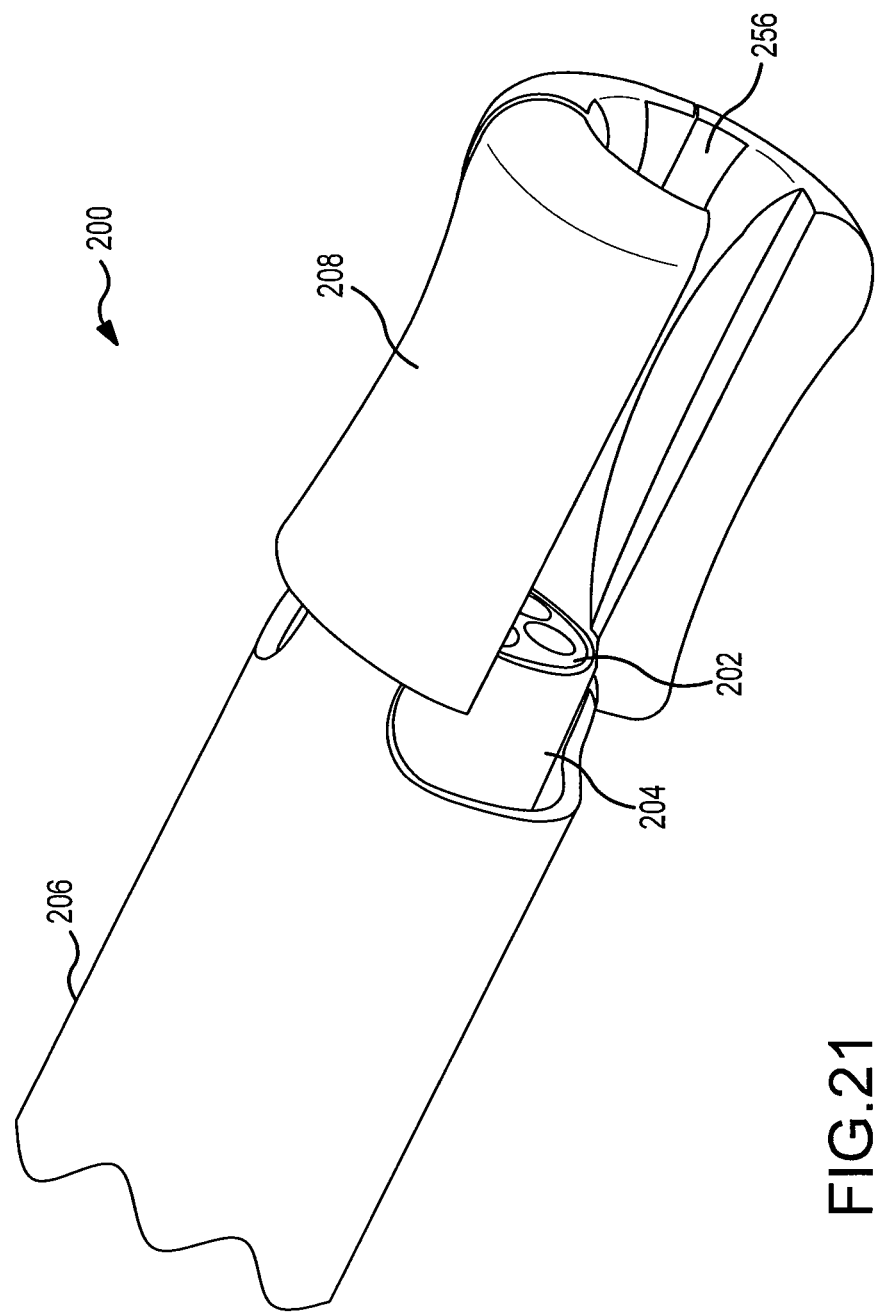
FIG. 21 is a perspective view of the embodiment of FIG. 17 in a down turned orientation.

FIG. 21 is similar to FIG. 20, but shows the ribbed arms 208 in a rotated orientation. This may be accomplished by rotating the entire instrument 200 or by rotating the housing 206 and ribbed arms 208 relative to the sleeve 204 and tubular body 202.

Figure 22:
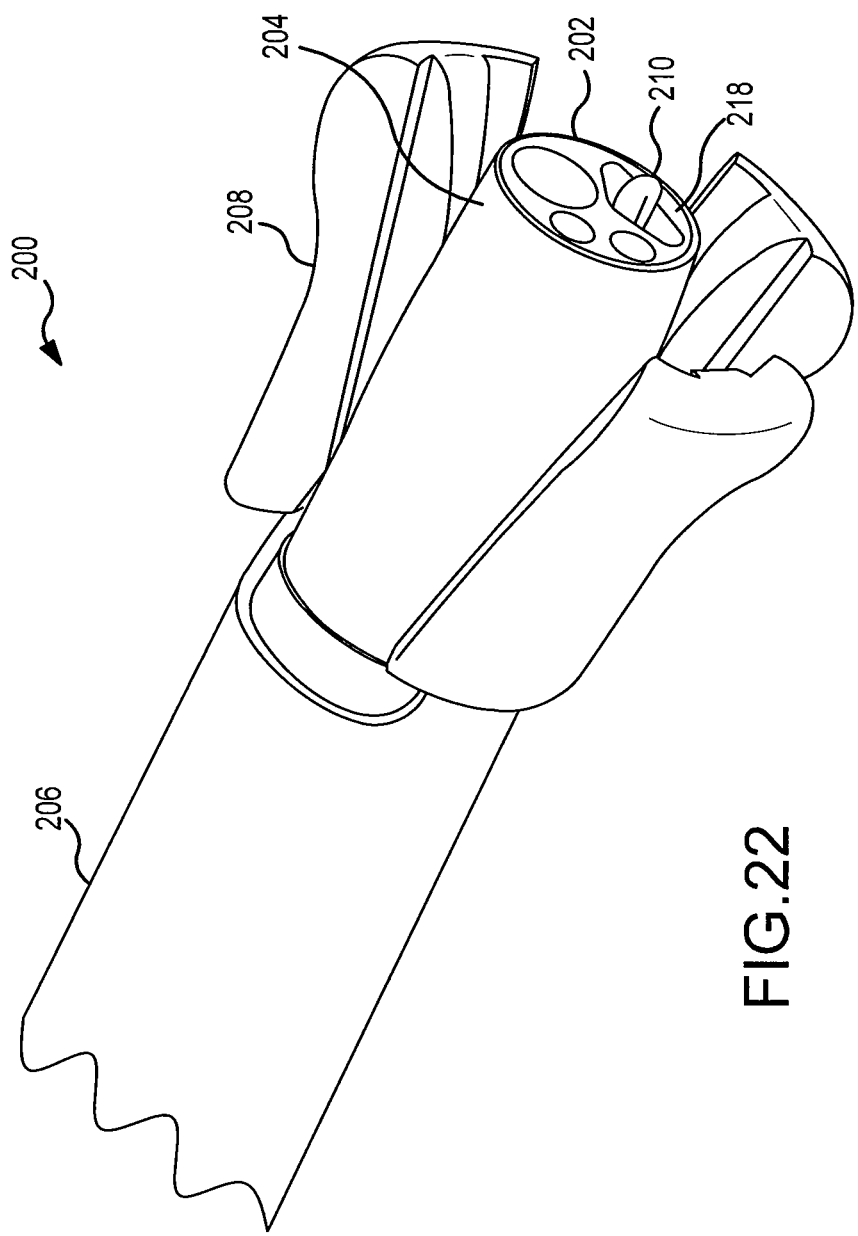
FIG. 22 is a perspective view of an instrument with an arm omitted and the arms in an open position according to certain embodiments.

FIG. 22 shows the tubular body 202 and sleeve 204 in an advanced position and the ribbed arms 208 in a resulting open or expanded position. As shown, as with FIGS. 20 and 21, a portion of the circumference around the instrument 200 is not guarded or protected by a ribbed arm 208 because it has been omitted. It is noted that the tip of a blade 210 with a longitudinal cutting direction is shown projecting slightly from a port 218 of the tubular member 202.

Figure 23:
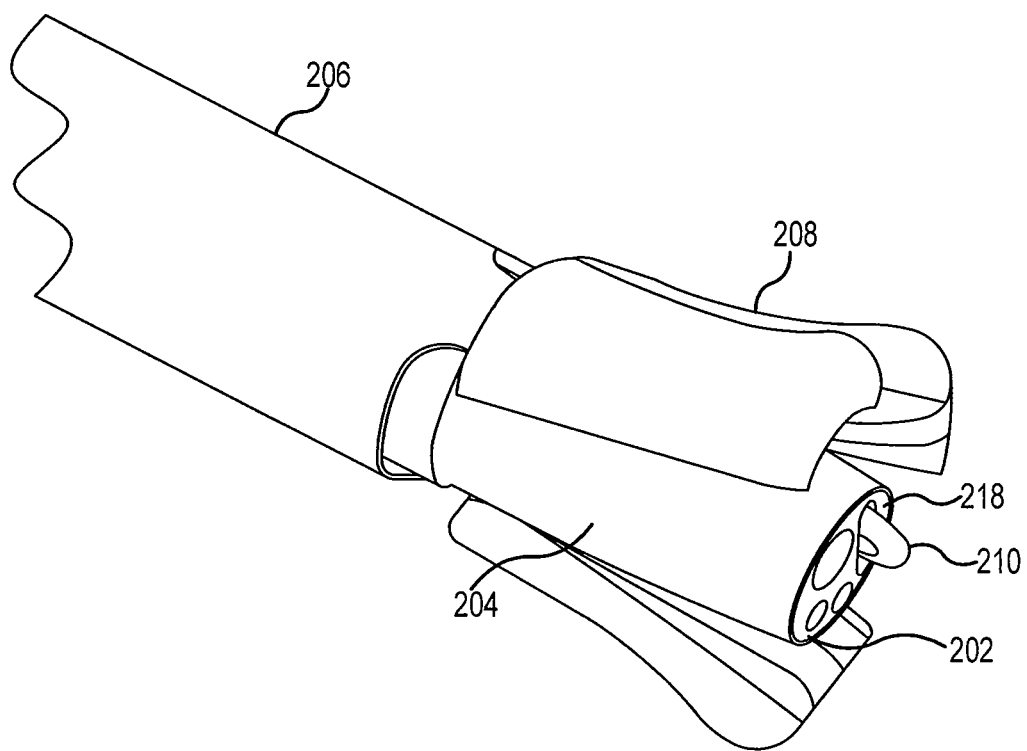
FIG. 23 is a perspective view of the embodiment of FIG. 19 in a down turned orientation.

FIG. 23 parallels FIG. 21 in that the ribbed arms 208 are in a rotated orientation. Like FIG. 22, the tubular body 202 and sleeve 204 are in an advanced position and the ribbed arms 208 are in a resulting open or expanded position. It is noted that the tip of a blade 210 with a transverse cutting direction is shown projecting slightly from a port 218 of the tubular body 202.

Figure 24:
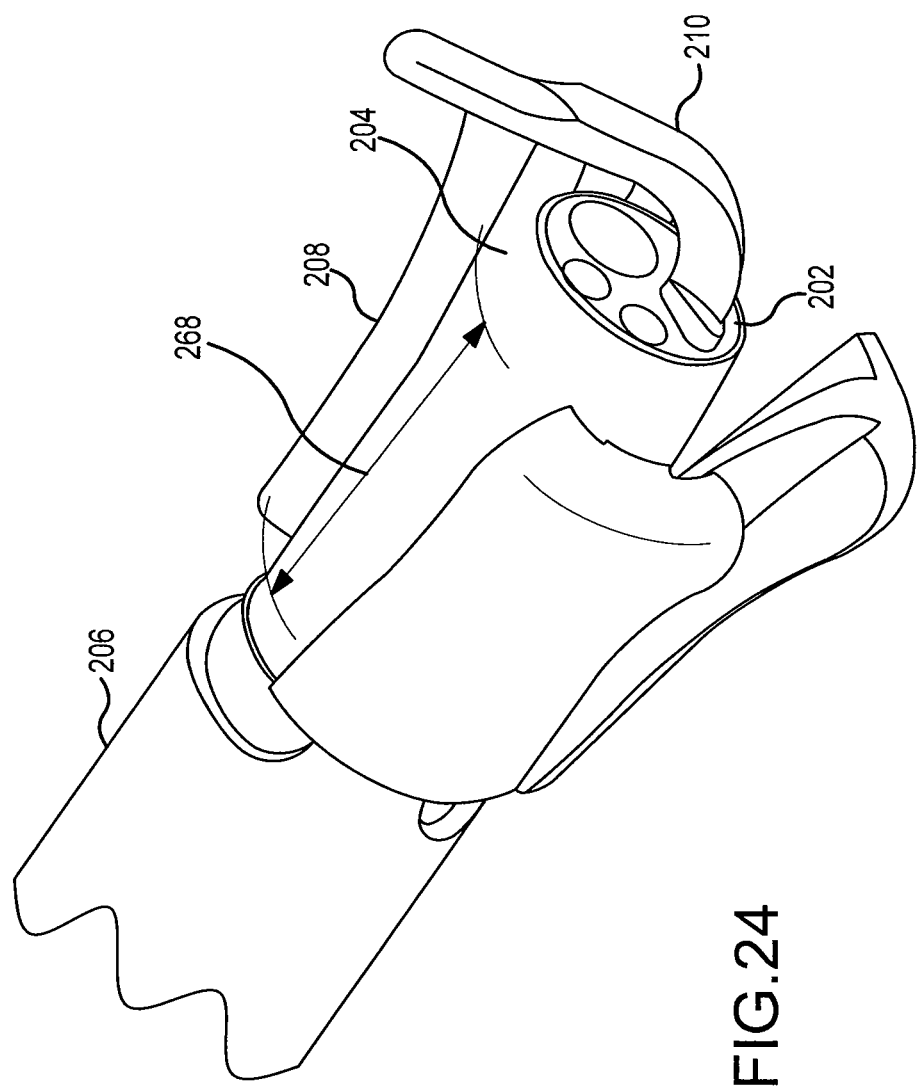
FIG. 24 is a perspective view of an instrument with an arm omitted, the arms in an open position, and a blade extended according to certain embodiments.

FIG. 24 is similar to FIG. 22, but shows the blade 210 extending from the tubular body 202. As shown, the blade tip is oriented in a longitudinal cutting direction and is further oriented relative to the ribbed arms 208 so as to be able to pass longitudinally through the channel 268 created due to the omitted ribbed arm 208. As such, depending on the curvature of the blade 210 and together with the telescoping nature of the tubular body 202 and sleeve 204, the working space 260 may include this channel 268 and may provide more freedom for surgical procedures in and around the ribbed arms 208.

Figure 25:
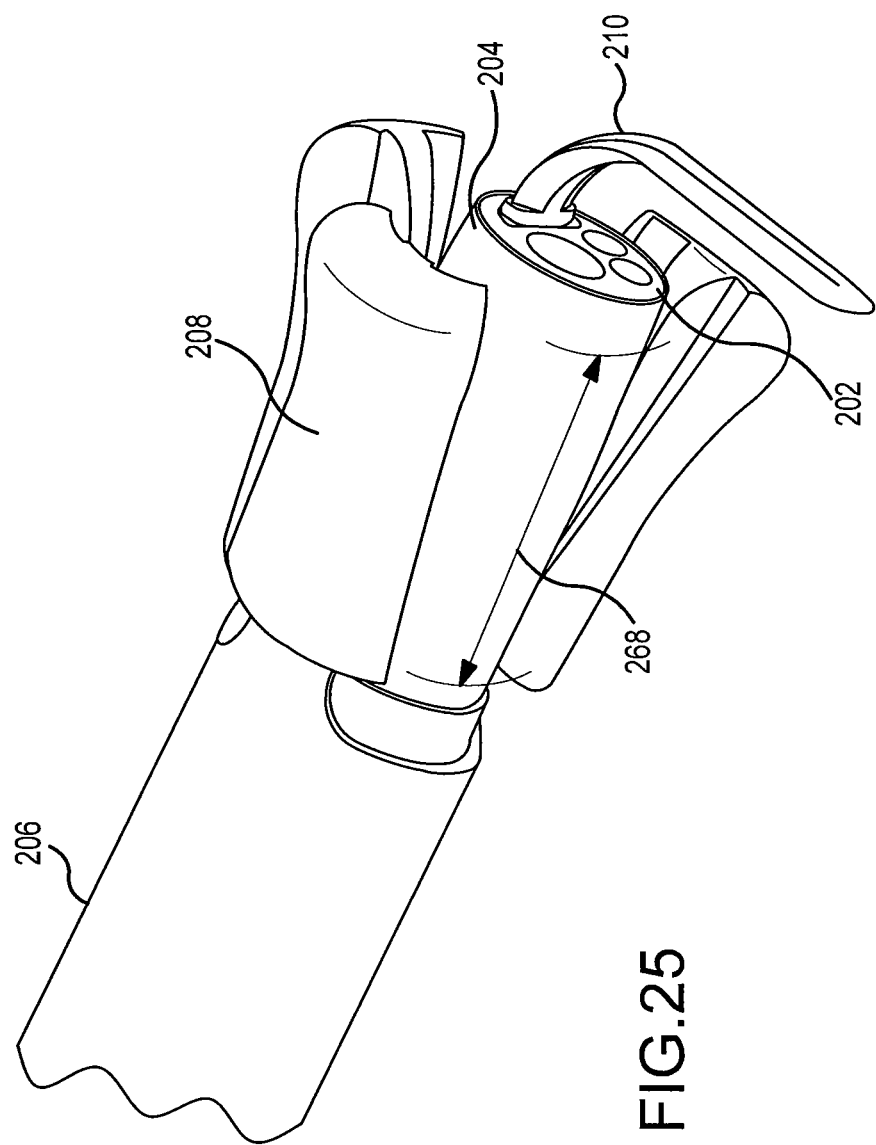
FIG. 25 is a perspective view of the embodiment of FIG. 21 in a down turned orientation.

FIG. 25 is similar to FIG. 23, but shows the blade 210 extending from the tubular body 202. As shown, the blade tip is oriented in a transverse cutting direction and like FIG. 24 is also oriented relative to the ribbed arms 208 so as to be able to pass longitudinally through the channel 268 created due to the omitted ribbed arm 208. As such, depending on the curvature of the blade 210 and together with the telescoping nature of the tubular body 202 and sleeve 204, the working space may include this channel 268 and may provide more freedom for surgical procedures in and around the ribbed arms 208.

Figure 26:
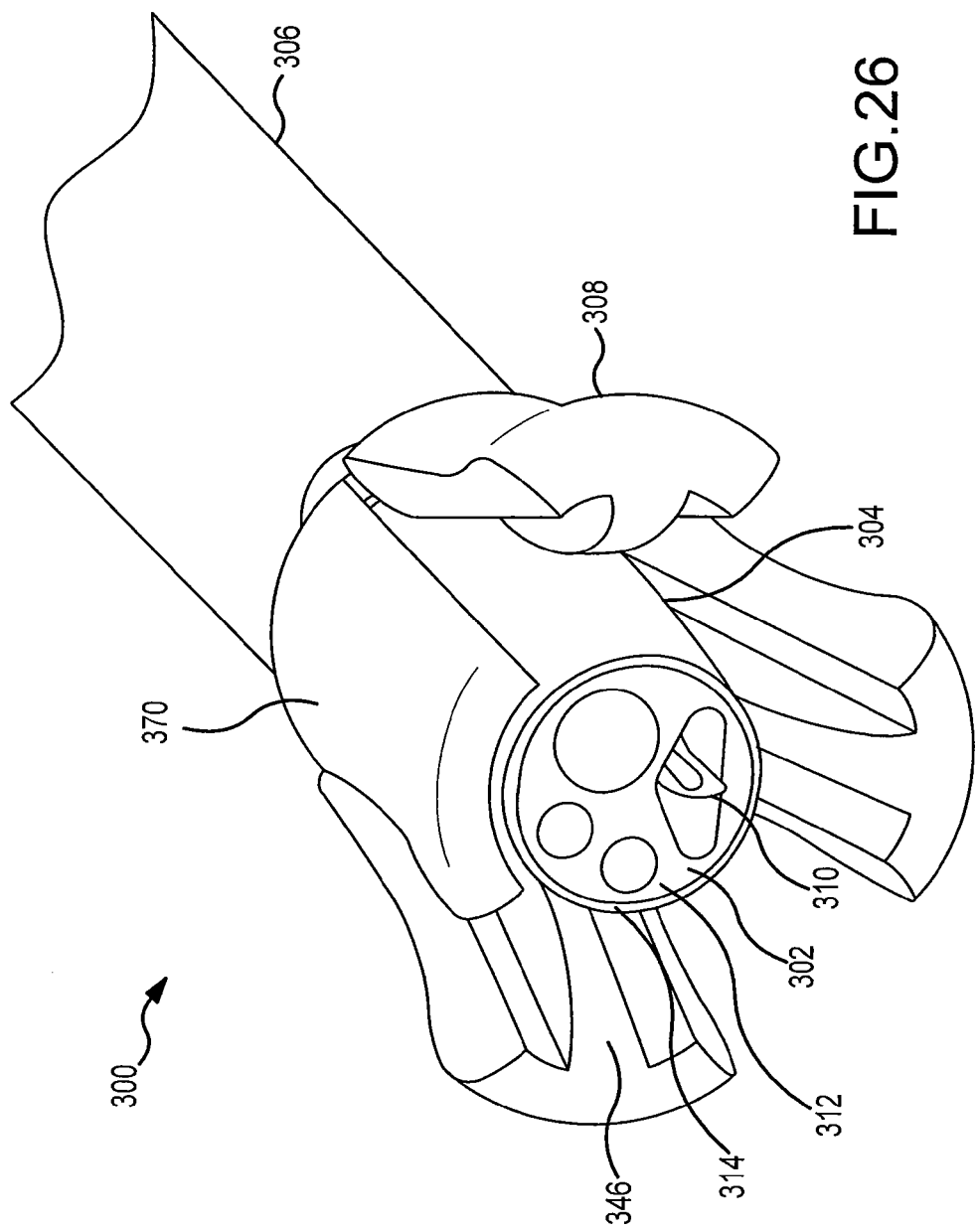
FIG. 26 is a perspective view of an instrument with three ribbed arms in their open position and a fourth non-ribbed arm in a close position according to certain embodiments.

FIGS. 26-30 show yet another embodiment. In FIG. 26 an instrument 300 is shown with three ribbed arms 308 and a single non-ribbed or lazy arm 370. As shown, the tubular body 302 and the sleeve 304 are shown in an advanced position with their distal ends 312, 314 approximately flush with the distal ends of the arms 308. However, as shown, only three of the arms 308 are in an expanded position and the fourth non-ribbed arm 370 is shown in a closed or collapsed position due to its lack of a rib 346. That is, without the rib on the arm 370, the advanced tubular body 302 and sleeve does not actuate the arm 370.

Figure 27:
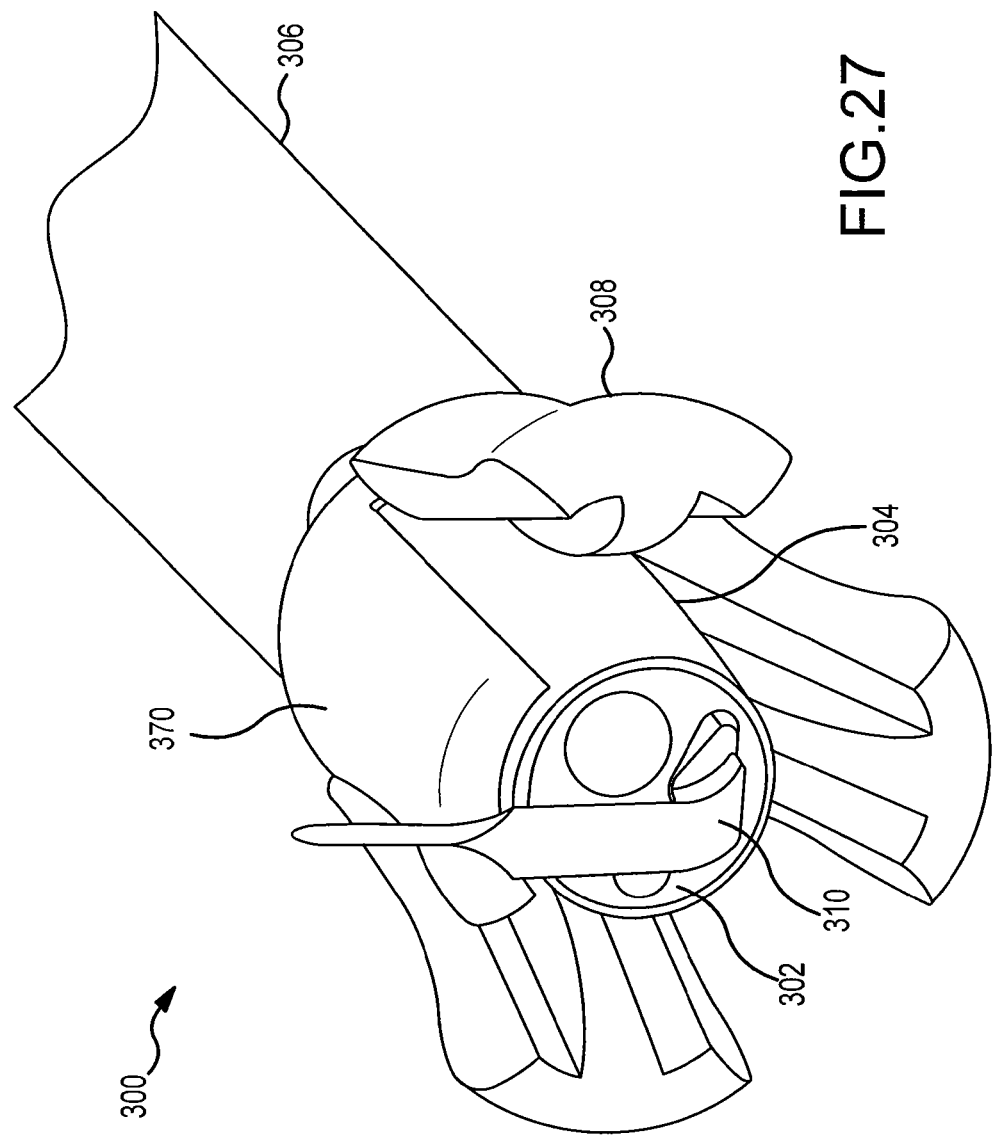
FIG. 27 is a perspective view of the embodiment of FIG. 23 with a blade extended.
Figure 28:
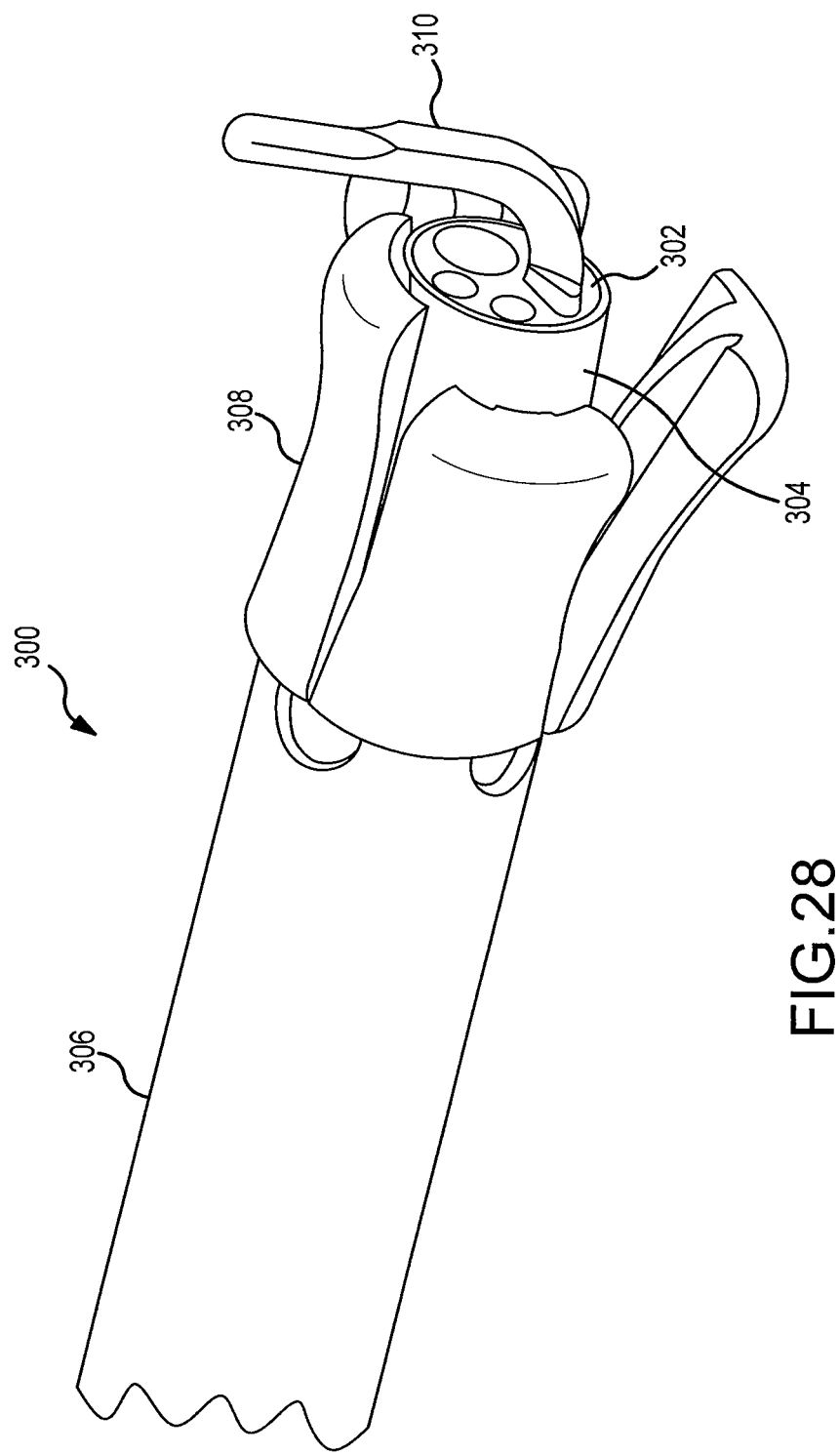
FIG. 28 is a perspective side view of the embodiment shown in FIG. 24.

FIG. 27 is similar to FIG. 26, but shows a longitudinal cutting blade 310 extended from a port 318 of the tubular body 302. FIG. 28 shows a perspective view of the position shown in FIG. 27.

Figure 29:
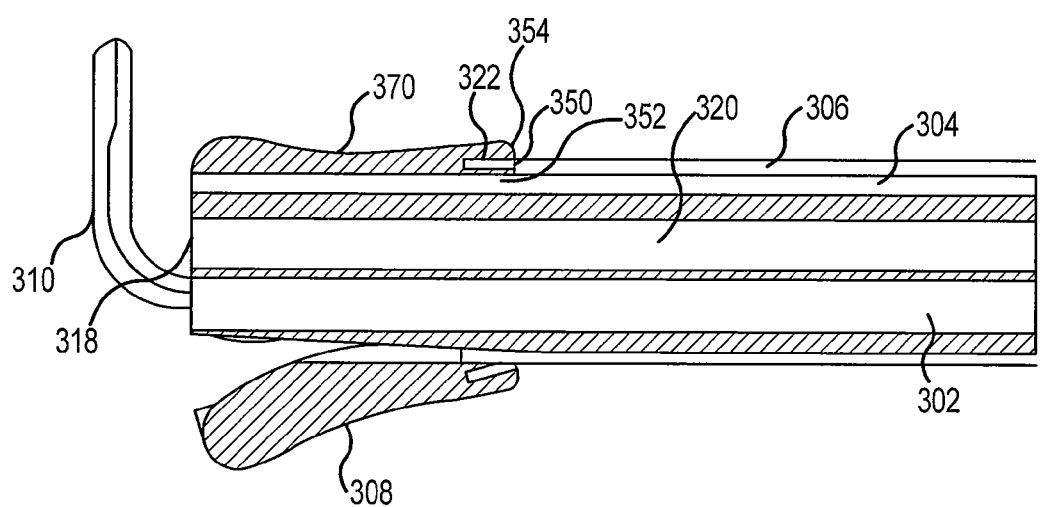
FIG. 29 is a cross-section view of the embodiment shown in FIGS. 24 and 25.

FIG. 29 shows a cross-section view of this embodiment in the position shown in FIGS. 27 and 28. The FIG. shows the tubular body 302 including one lumen 320 in this particular cross-section and the sleeve 304. The FIG. also shows one of the ribbed arms 308 in an expanded position and the lazy arm 370 positioned adjacent the advanced tubular body 302 and sleeve 304. It is noted that the slit 350 in the proximal end of the arms 308,370 is shown and the inner 352 and outer 354 shell of the slit 350 are also evident from this cross-section. Like FIGS. 27 and 28, the longitudinal cutting blade 310 is extended from the tubular body 302.

Figure 30:
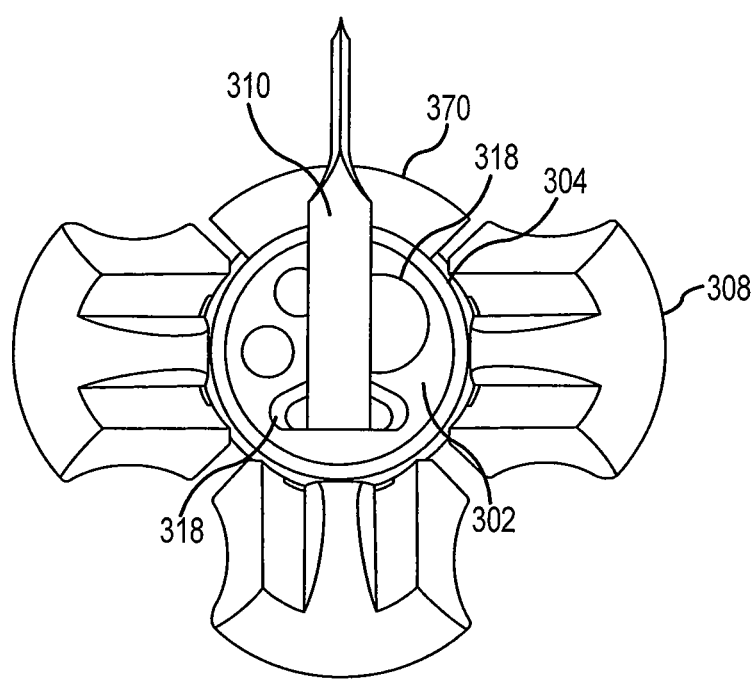
FIG. 30 is a distal view of the embodiment shown in FIGS. 24, 25, and 26.

FIG. 30 shows a distal end view of this embodiment. Similar to that shown in FIG. 6, the blade port 318 is shown offset slightly from the scope port 318 to facilitate viewing the proximal side of the blade 310 and beyond the blade 310.

In use, the instrument herein described may be used for several surgeries including open or closed surgeries. The instrument may be effectively used in minimally invasive procedures in constrained spaces. The instrument may be applied to arthroscopic procedures in several joints including the hip, knee, elbow, ankle, shoulder, and wrist. The instrument may also be applied to endoscopic procedures in various spaces containing nerves, tendons, ligaments, and fascia, including the hand, foot, intervertebral spaces, and especially the carpal tunnel of the wrist and hand, the cubital tunnel, and the tarsal tunnel. The instrument may be useful for improving visualization in internally performed procedures in which the instrument is inserted through a small incision to facilitate the manipulation of specific tissues and structures in the body. In one embodiment, the instrument may be used to perform a carpal tunnel release (CTR) procedure for carpal tunnel syndrome. In another embodiment, the instrument may be used to perform ulnar nerve decompression for cubital tunnel syndrome.

Figure 31:
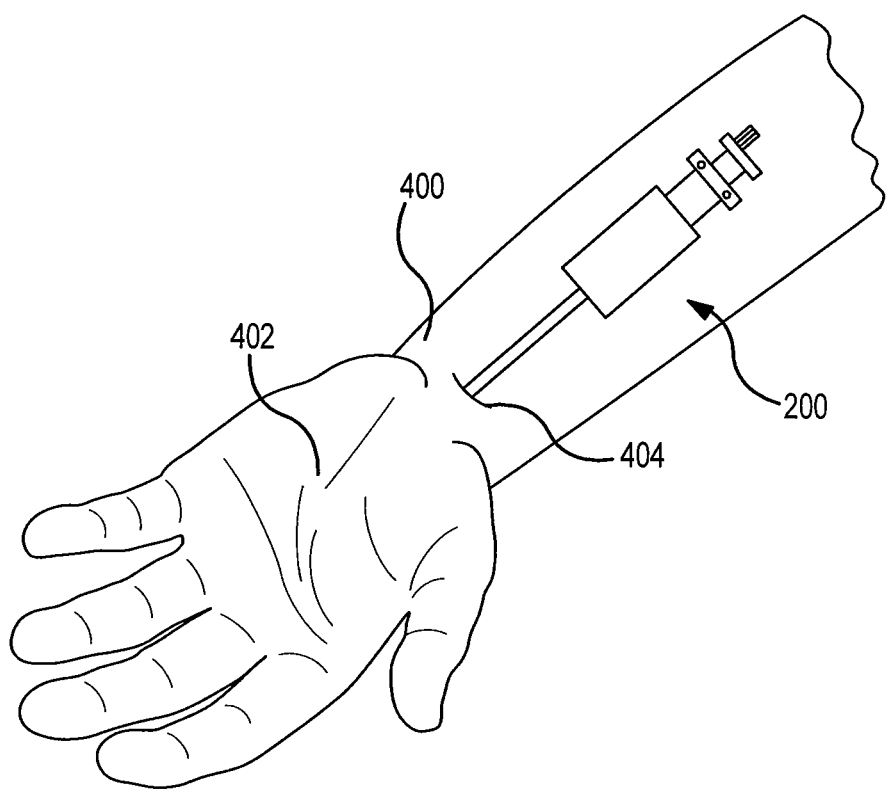
FIG. 31 is a perspective view of a carpal tunnel release procedure according to certain embodiments.

The CTR procedure will now be described with reference to FIG. 31. Similar to traditional open CTR surgery, endoscopic CTR surgery may be performed under local, regional, or general anesthesia. The procedure may be performed by placing an incision 404 in the wrist 400 or the palm 402 or both. The incision 400 may penetrate the through the skin and any subcutaneous fat below the skin down to the antibrachial fascia. A small transverse incision may then be made through the antibrachial fascia to expose the bersa. Then the antibrachial fascia may be opened up longitudinally and distally. A synovial elevator may be used to elevate the synovium and locate the underside of the transverse carpal ligament. Once located, the synovium can continue to be elevated from the transverse carpal ligament to allow appropriate visualization. The instrument described herein may then be inserted with the arms in the closed or collapsed position.

In one embodiment, the instrument 200 shown and described with respect to FIGS. 17-22 may be used. A pressure detection device may be provided through at least one of the ports 218 of the instrument 200 and the pressure in the tunnel may be measured prior to transecting the ligament. In this embodiment, the instrument 200 may be positioned so the channel 268 where the ribbed arm 208 has been omitted is facing upward toward the bottom side of the transverse carpal ligament. It is noted here that rotational motion of the tubular body 202 and sleeve 204 relative to the housing 206 and the ribbed arms 208 is advantageous because of the ability to position each appropriately for the procedure. Moreover, once the ribbed arms 208 have been expanded, the tubular body 202 and sleeve 204 and thus the blade 210 can continue to be manipulated and moved without moving the ribbed arms 208 and causing undue abrasion and trauma to surrounding tissues. The ribbed arms 208 may be specifically placed to retract and thus protect non-target anatomy such as the median nerve or palmer arterial structures. Having placed the instrument 200 with the channel 268 facing the transverse carpal ligament, a blade 210 with a longitudinal facing cutting edge may be used to sever the ligament. That is, as the blade 210 is extended out of the port 218 of the tubular body 202, the blade's curvature may be such as to cause the blade 210 to extend upward and penetrate the ligament. Longitudinal motion of the instrument 200 and/or longitudinal motion of the tubular body 202 and/or sleeve 204 relative to the instrument 200 may cause the blade 210 to cut the ligament. The pressure detection device may then be used to measure the pressure in the tunnel.

Those skilled in the art will understand and appreciate the various approaches known in the art for performing a carpal tunnel release procedure. As such, use of the described embodiment as well as other embodiments of the instrument herein described will be apparent to those having skill in the art. Moreover, varying incision locations and procedures surrounding accessing and severing the ligament will also be apparent to those having skill in the art. These variances may be based on the surgeon's preference. The incision location may be in the flexion crease of the wrist as described above or may in the palm of the hand. The instrument may be inserted through a longitudinal (elongated) or transverse (wide) surface incision. The orientation of the cutting blade may be manipulated so that it is pointing up, as described above, to separate the TCL from underneath (the "inside out" approach) or pointing down to separate the TCL from above (the "outside in" approach). In this "outside in" approach, the procedure may be performed open or an extraligamentous approach may be used where the operative space for placement of the device would be between the skin and the transverse carpal ligament in the subcutaneous space. The retractors and elevators may develop the subcutaneous space. With blade activation the transverse carpal ligament may be cut and the contents of the carpal canal including median nerve may be visualized beyond the transverse carpal ligament. The type of blade used and the direction of the sharp cutting edge may vary. Depending on the direction of the cutting edge, the location of its insertion (proximal or distal to the TCL), the TCL may be cut in a distal to proximal or proximal to distal direction. Depending on the thickness of the TCL and the thickness and sharpness of the blade, more or fewer passes of the blade may be required to completely release the TCL.

Figure 32:
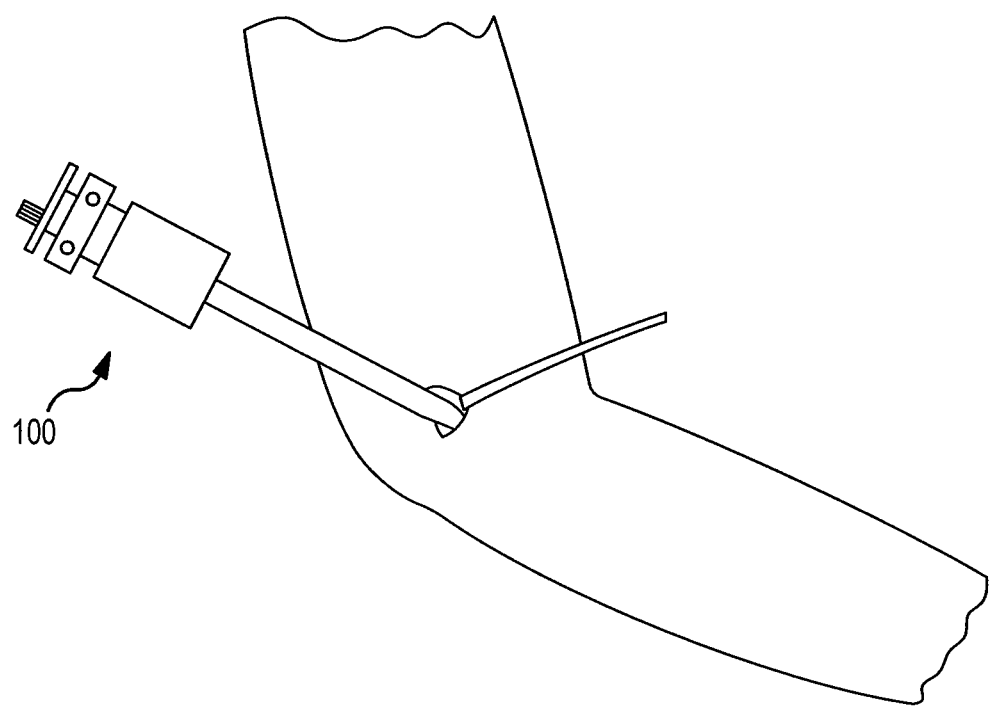
FIG. 32 is a perspective view of an ulnar nerve decompression procedure according to certain embodiments.

The cubital tunnel decompression procedure will now be described with reference to FIG. 32. First, a brachial plexus nerve block may be used with lidocaine and buvipacaine and a tourniquet may be placed on the arm. The arm may be positioned in 90° abduction with the forearm supinated and the elbow flexed to 120°. The medial epicondyle may face anteriorly while the lateral epicondyle is supported by a stack of towels. Second, a 2-3 cm curvilinear longitudinal incision may be made between the medial epicondyle and the olecranon along the path of the ulnar nerve. The small incision size of the endoscopic procedure may be contrasted with the 6 cm (for simple decompression) to up to 15 cm (for transposition and medial epicondylectomy) incision sizes required in non-endoscopic surgical methods. Third, the incision may be deepened until the fascia of the flexor carpi ulnaris and Osborne's ligament (also called the cubital tunnel retinaculum) are exposed. Upon recognition, the flexor carpi ulnaris fascia and Osborne's ligament above the cubital tunnel may be cut to expose the ulnar nerve. Fourth, the retractor device may be inserted between the subcutaneous tissue and the superficial forearm fascia overlying the flexor carpi ulnaris. Fifth, an instrument as described herein may be introduced distally between the flexor carpi ulnaris muscle and the two heads of the flexor carpi ulnaris. Sixth, the arms of the instrument may be expanded to facilitate visualization and access to target structures. Seventh, an endoscopic camera included within a lumen of the tubular body of the instrument may be advanced to directly visualize the overlying fascia, the flexor carpi ulnaris muscle, and the ulnar nerve. Eighth, a blade may be advanced from the distal end of the instrument for releasing all possible sites of compression within the cubital tunnel under direct visualization projected to a monitor from the endoscopic camera. The following sites may be divided with the blade to decompress the ulnar nerve: (i) the overlying fascia of the flexor carpi ulnaris muscle, (ii) Osborne's ligament (the cubital tunnel retinaculum) when present, (iii) the flexor pronator aponeurosis, (iv) the medial intermuscular septum, (v) the edge of the triceps, and (vi) the arcade of Struthers. Ninth, upon completion of the release of all potential sites of compression in the cubital tunnel in a range of up to 10 cm on each side of the medial epicondyle, the elbow may be brought through a full range of motion to determine whether there is any subluxation of the nerve. If subluxation is present a medial epicondylectomy may be performed through the same incision site during the same exposure. To conclude the endoscopic procedure, the tourniquet may be released, hemostatis obtained, and fine nylon sutures may be put in place as necessary. A soft elbow dressing may be applied and the patient may be encouraged to move the elbow on the first post-operative day. (See Tsai, et al. "Cubital Tunnel Release With Endoscopic Assistance: Results of a New Technique" *The Journal of Hand Surgery*, Vol. 24A No. 1 January 1999.)

In the above procedure, while not limited to this list, any of the following anatomical structures may be displaced or protected by the retractor arms: ulnar nerve, median nerve, radial nerve, fascia, arcade of Struthers, medial epicondyle, lateral epicondyle, flexor carpi ulnaris muscle, pronator muscle, triceps muscle, biceps muscle, anconeus epitrochlearis muscle, cubital tunnel retinaculum, anterior medial collateral ligament, ulnar collateral ligament, annular ligament of radius, biceps tendon, common extensor tendon, olecranon, humerus, radius, and ulna.

A transducer may be used during the procedure to ensure that ischemic nerve damage is avoided. The transducer monitors the mechanical effects produced in a nerve in response to the pressures to which a nerve is subjected by the manipulation of instruments during surgery. The transducer may either be placed externally, outside of the body, or internally through a port of the endoscope or arthroscope.

The presently described instrument and methods are advantageous for several reasons that will now be discussed in detail. First, the instrument may allow for reallocating an already fixed amount of space where known expansion devices may be ineffective due to surrounding constraining tissue or anatomical structures. That is, the device may allow for displacing tissue by selectively expanding the arms and, where necessary, further rotating and/or longitudinally displacing the arms and thus the tissue. This leads to another advantage, which is that the tubular body and associated ports and devices may be moved both rotationally and longitudinally relative to the arms. As such, while the tissue is displaced, the procedure may continue without being limited by the manner in which the tissue is displaced. In turn, the surgeon may be able to make a more precise incision and minimize the time required for reparative sealing and the potential for scar tissue growth.

The above advantages may minimize abrasion to nearby tissues because the arms may stay positioned without needing to be moved to accommodate the procedure. In addition, the gently curved or rounded distal tips of the arms disclosed herein are in contrast to other known devices with sharp angles that may damage surrounding tissues. As such, the instrument may be used in close proximity to sensitive anatomical structure while the blade is used to cut nearby structures. For example, the arm, with its soft, resilient, protective barrier may be aligned with the median nerve while the blade is aligned with the TCL.

Additionally, longitudinal advancement of the housing by rotation rather than by sliding movement may also facilitate a more refined incremental extension of the sleeve. That is, the housing may be rotated so as to move longitudinally. The degree of longitudinal motion is thus controlled and concern for abrupt longitudinal slippage may be minimized.

The above advantages are provided without the rupture risks associated with known inflatable retractors. Moreover dissection may be avoided and the abrasion to near by tissues may be avoided.

An additional advantage of the present device is the common motion between the soft protective arm sheath and the arms themselves. Concerns over remembering to deploy an inflatable member for protection prior to extending, retracting, or radially adjusting the arms are not pertinent, because the protective sheath is expanded and contracted together with the arms and is thus always appropriately positioned to protect surrounding tissues and structures.

Additionally, the arms may exist in a variety of shapes, sizes, and patterns in order to permit retraction of tissue and structures in an array of directions and in a manner not limited to planar dissection. The ribbed design shown in FIGS. 7-27 is mechanically advantageous because it provides a relatively high degree of control of the position of the arms.

Those of skill in the art will understand and appreciate that several modifications may be made to the above description and still remain within the scope of the disclosure. For example, the instrument described may be provided as part of a complete unitary endoscopic or arthroscopic system or it may be provided as part of a separate component compatible with other single-port, dual-port, and multi-port endoscopes or arthroscopes and for use with other endoscopic or arthroscopic instruments. The retracting portion of the instrument may be provided as a housing as discussed in the FIGS. above. Alternatively, the retracting portion may be provided as a solid tubular member rotatably mounted within an internal channel of a cannula, endoscope, or arthroscope, where the arms may extend from its distal end.

With respect to all disclosed embodiments, the number of arms may include any number of arms. The spacing between the arms may be such that, in their closed or collapsed position, adjacent arms abut against one another. Alternatively, spaces between the arms may be provided. The shape of the arms may be any shape. While the gentle curves and non-sharp edges of the described embodiments may be advantageous, other types of arms are within the scope of the disclosure.

The size of the device may cover a wide range and may depend on the type of surgery it is adapted for. This may include larger diameters for more robust surgeries in more open spaces and smaller diameters for more delicate surgeries in more constrained spaces. This may also include longer or shorter instruments depending on the distance the distal end of the device travels. The material of the device may be adapted based on the flexibility or rigidity appropriate for a given type of use. Any combination of these modifications may be included and considered with one another for providing a suitable instrument.

The arms of the instrument may be collectively actuatable or selectively actuatable. That is, one, two, or more arms may be actuated while others are left in a closed or contracted position. This may occur as a result of certain arms not having ribs as shown in FIGS. 23-27 or it may occur due to an actuation device capable of selectively choosing to actuate some arms and not others.

The instrument may be made of disposable materials or reusable materials. Moreover, depending on the level of incorporation of the retracting elements into an endoscope, arthroscope, or other medical device, portions of the instrument may be disposable and others reusable.

Although the present invention has been described with reference to preferred embodiments, persons skilled in the art will recognize that changes may be made in form and detail without departing from the spirit and scope of the invention.

What is claimed is:

1. A medical instrument for minimally invasive surgery comprising
   an outer housing having a tubular shape, a distal end and a proximal end, and defining a longitudinal axis;
   a tubular body positioned within the outer housing and configured to slide longitudinally with respect to the outer housing;
   a sleeve positioned between the outer housing and the tubular body and configured to slide longitudinally with respect to both the outer housing and the tubular body, wherein the sleeve tapers in thickness from an intermediate longitudinal location to a distal end;

a plurality of retractor arms extending from the distal end of the outer housing and coupled to the distal end of the outer housing via respective hinged connections, wherein each of the retractor arms defines a convex curved rib extending radially inward from and along a longitudinal length of an inner surface of each of the retractor arms;

an additional retractor arm extending from the distal end of the outer housing and coupled to the distal end of the outer housing via a respective hinged connection, wherein the additional retractor arm has a smooth inner surface with no rib; and a first actuation mechanism attached to the sleeve and configured to move the sleeve longitudinally with respect to the outer housing; wherein longitudinally advancing the sleeve distally with the first actuation mechanism causes an outer surface of the sleeve to slide along the convex curved ribs thereby expanding each of the retractor arms radially outward relative to the longitudinal axis.

2. The medical instrument of claim 1, wherein the distal end of the outer housing defines a plurality of distally extending tabs and a base of each of the retractor arms and the additional retractor arm define a slit for receiving respective tabs of the plurality of distally extending tabs to form the hinged connections.

3. The medical instrument of claim 2, wherein
the base of each of the retractor arms defines an inner shell portion that defines a portion of the respective slit; and
the sleeve further defines a stepped down portion adjacent to and proximal to the intermediate longitudinal location that forms an annular shelf that interfaces with a proximal edge of the inner shell portion when the plurality of retractor arms are fully extended radially outward.

4. The medical instrument of claim 1, wherein the convex curved rib of each of the retractor arms is oriented substantially normal to the inner surface of the retractor arm.

5. The medical instrument of claim 1, wherein the tubular body is configured to extend telescopically beyond a distal end of the sleeve.

6. The medical instrument of claim 1, wherein the tubular body is further configured to rotate with respect to the outer housing.

7. The medical instrument of claim 1, wherein the sleeve is configured to rotate with respect to both the outer housing and the tubular body.

8. The medical instrument of claim 1, wherein the tubular body is an endoscope or arthroscope.

9. The medical instrument of claim 8, wherein the tubular body has an internal lumen for receiving and passing through a medical device.

10. The medical instrument of claim 9, further comprising a blade positioned within and configured to extend distally from the internal lumen.

11. The medical instrument of claim 10, wherein the tubular body is rotatable relative to the outer housing and the sleeve to facilitate positioning of the blade without rotating the outer housing and the plurality of retractor arms associated therewith.

12. The medical instrument of claim 10, wherein
the plurality of retractor arms and the additional retractor arm are positioned in a radial array around a perimeter of the distal end of the outer housing;
the radial array has a number of equally spaced positions equal to the number of the plurality of retractor arms and the additional retractor arm plus an additional position without a retractor arm; and
the additional position provides an increased working space for the blade.

13. The medical instrument of claim 1, wherein an outer surface of each of the retractor arms is formed as a smooth, nonabrasive surface.

14. The medical instrument of claim 13, wherein the outer surface of each of the retractor arms is formed as a convex curve to define an hourglass shape.

15. The medical instrument of claim 14, wherein a distal edge of the outer surface of each of the retractor arms is radiused.

16. The medical instrument of claim 1, wherein the plurality of retractor arms and the additional retractor arm are equally spaced around a perimeter of the distal end of the outer housing.

17. The medical instrument of claim 16, wherein the plurality of retractor arms and the additional retractor arm define a lumen when in a closed position.

18. The medical instrument of claim 1, wherein
the outer housing defines a plurality of guide lumens corresponding to each of the retractor arms and the additional retractor arm and extending from a proximal location on the outer housing to the distal end of the outer housing; and
the medical instrument further comprises
a plurality of guide wires respectively extending through each of the guide lumen and attached to each of the retractor arms and the additional retractor arm; and
a second actuation mechanism attached to proximal ends of the guide wires and configured to individually and collectively pull and push the guide wires to cause distal ends of each of the retractor arms and the additional retractor arm to pivot radially outward and inward relative to the longitudinal axis.

19. The medical instrument of claim 18, wherein the second actuation mechanism controls the plurality of retractor arms and the additional retractor arm independently of the first actuation mechanism.

* * * * *